(12) United States Patent
Kozikowski et al.

(10) Patent No.: US 7,244,855 B2
(45) Date of Patent: Jul. 17, 2007

(54) SYNTHESIS OF OLIGOMERIC EPICATECHIN AND CATECHIN-DERIVED PROCYANIDINS

(75) Inventors: Alan P. Kozikowski, Chicago, IL (US); Werner Tückmantel, Tucson, AZ (US); Leo J. Romanczyk, Jr., Hackettstown, NJ (US); Xingquan Ma, Chicago, IL (US)

(73) Assignee: Mars, Inc.

( * ) Notice: Subject to any disclaimer, the term of this patent is extended or adjusted under 35 U.S.C. 154(b) by 392 days.

(21) Appl. No.: 10/481,729

(22) PCT Filed: Oct. 2, 2003

(86) PCT No.: PCT/US03/31375

§ 371 (c)(1),
(2), (4) Date: Sep. 15, 2004

(87) PCT Pub. No.: WO2004/030440

PCT Pub. Date: Apr. 15, 2004

(65) Prior Publication Data
US 2005/0020512 A1    Jan. 27, 2005

Related U.S. Application Data

(63) Continuation-in-part of application No. 10/658,241, filed on Sep. 9, 2003, now Pat. No. 7,067,679.

(60) Provisional application No. 60/415,616, filed on Oct. 2, 2002.

(51) Int. Cl.
C07D 311/00    (2006.01)
(52) U.S. Cl. ..................... 549/399; 514/453
(58) Field of Classification Search ............... 549/399; 514/453
See application file for complete search history.

(56) References Cited

U.S. PATENT DOCUMENTS

| | | | | |
|---|---|---|---|---|
| 4,255,336 | A | 3/1981 | Albert et al. | 260/345.2 |
| 4,644,011 | A | 2/1987 | Ballenegger et al. | 514/456 |
| 5,554,645 | A * | 9/1996 | Romanczyk, Jr. et al. | 514/453 |
| 6,156,912 | A | 12/2000 | Tuckmantel et al. | 549/399 |
| 6,207,842 | B1 | 3/2001 | Romanczyk, Jr. et al. | 549/399 |
| 6,420,572 | B1 | 7/2002 | Romanczyk, Jr. et al. | 549/400 |
| 6,476,241 | B1 | 11/2002 | Kozikowski et al. | 549/399 |
| 6,528,664 | B2 | 3/2003 | Romanczyk et al. | 549/400 |
| 6,720,432 | B2 | 4/2004 | Kozikowski et al. | 549/415 |
| 2003/0114691 | A1 | 6/2003 | Romanczyk et al. | 549/354 |
| 2003/0176620 | A1 | 9/2003 | Romanczyk et al. | 528/86 |
| 2004/0116718 | A1 | 6/2004 | Kozikowski et al. | 549/403 |
| 2004/0176441 | A1 | 9/2004 | Romanczyk et al. | 514/456 |

FOREIGN PATENT DOCUMENTS

| | | |
|---|---|---|
| DE | EP 0039844 | 11/1978 |
| EP | DE 15 18 003.7 | 1/1969 |
| EP | 0096 007 | 5/1983 |
| EP | 0216936 | 4/1987 |
| JP | 58-154571 | 9/1983 |
| JP | 62-48677 | 3/1987 |
| JP | 41 90774 | 11/1990 |
| WO | WO 90/13304 | 11/1990 |
| WO | WO 97/36597 A | 10/1997 |

OTHER PUBLICATIONS

U.S. Appl. No. 09/292,244, filed Apr. 15, 1999, Basak et al.
U.S. Appl. No. 10/481,729, filed Dec. 22, 2003, Kozikowski et al.
U.S. Appl. No. 10/783,801, filed May 28, 2004, Kozikowski et al.
Balde, A.M. et al., Phytochemistry, vol. 30, No. 12, p. 4129-4135 (1991).
Botha, J.J. et al, J. Chem. Soc. Perkin I, 1235-1245 (1981).
Botha, J.J. et al, J. Chem. Soc. Perkin I, 527-533 (1982).
Buffnoir et al., Third Tannin Conference Bend Oregon , pp. 15-16 (1998).
Chu, S.C. et al, J. of Natural Products, 55, (2), 179-183 (1992).
Delcour, J.A. et al, J. Chem. Soc. Perkin Trans I 1711-1717 (1983).
Deschner, E.E. et al, Carcinogenesis, 7, 1193-1196, (1991).
Dess et al., J. Am. Chem. Soc. vol. 113, pp. 7277-7287 (1991).
Ferriera, D. et al, Tetrahedron, 48, (10), 1743-1803 (1992).
Foo, L.Y. et al, J. Chem. Soc. Perkin I 1983:1535-1543.

(Continued)

Primary Examiner—Kamal A. Saeed
Assistant Examiner—Rei-tsang Shiao
(74) Attorney, Agent, or Firm—Margaret B. Kelley; Gibbons P.C.

(57) ABSTRACT

Various processes are disclosed for preparing procyanidin oligomers having (4,8)-interflavan linkages. In an improved process, a tetra-O-protected-epicatechin or -catechin monomer or oligomer is coupled with a protected, C-4 alkoxy-activated-epicatechin or -catechin monomer in the presence of an acidic clay instead of a Lewis acid. In a second process, a 5,7,3',4'-tetra-O-protected or preferably penta-O-protected-epicatechin or -catechin monomer or oligomer is reacted with a tetra-O-protected or preferably penta-O-protected-epicatechin or -catechin monomer having a thio activating group at the C-4 position; the coupling is carried out in the presence of silver tetrafluoroborate. In third process, two molecules of a penta-O-protected-epicatechin or -catechin monomer activated with a 2-(benzothiazolyl) thio group at the C-4 position are self-condensed in the presence of silver tetrafluoroborate. An improved two-step process for preparing a C-4 alkoxy activated tetra-O-benzyl-protected, 8-bromo-blocked-epicatechin or -catechin monomer is also provided. The use of naturally-derived and synthetically-prepared procyanidin $(4\beta,8)_4$-pentamers to treat cancer is also disclosed.

5 Claims, No Drawings

OTHER PUBLICATIONS

Foo, L.Y. et al, *J. Chem. Soc.*, Chem. Commun., 85-86 (Sep. 1984).
Funayama, M. et al, *Biosci. Biotech. Biochem.*, 58, (5), 817-821 (1994).
Ho, C.T., Lee C.Y., and Huang, M.T. Eds., Phenolic Compounds in Foods and Their Effects on Health I. Analysis, Occurrence and Chemistry, ACS Symposium Series 506, American Chemical Society, Washington D.C. (1992).
Hundt, H.K. et al, *J. Chem. Soc.* Perkin I: 1227-1234 (1981).
Ireland et al., J. Org. Chem , vol. 58, p. 2899 (1993).
Kato, R. et al, Carcinogenesis, 1301-1305 (1983).
Kawamoto, H, et al. Synthetic Communications, 26(3), 531-534 (1996).
Kawamoto, H. et al, Mokazai gakkaishi, 37, (5) 488-493 (1991).
Keogh et al, Chem. Ind. (London) 2100-1 (1961). Abstract only.
Khanbabaee, K. et al, Tetrahedron, 53:31, 10725-10732 (1997).
Kiatgrajai P., et al. *J. Org. Chem.* 47, 2910-2012 (1982).
Kitao et al, *Biosci. Biotech. Biochem.* 59(11), 2167-2169, (1995).
Kolodziej, H., Phytotherapy Research, 9:410-415 (1995).
Kozikowski et al., "Studies in Polyphenol Chemistry and Bioactivity. 3.[1,2] Stereocontrolled Synthesis of Epicatechin-4α,8-epicatechin, an Unnatural Isomer of the B-Type Procyanidins", J. Org. Chem., 2001.
Kozikowski, A, et al. J. Org. Chem., 65, 5371-5381 ( 2000).
Meyer, S., *J. Org. Chem.*, 59: 7549-7552 (1994).
Newman, R.H., Magnetic Resonance in Chemistry 25:118-124 (1987).
Nonaka, G-I., *Chem. Pharm. Bull.* 31 (11) 3906-3914 (1983).
Nonaka G-I., et al. *J. Chem. Soc.* Perkin Trans., I: p. 2139-2145 (1983).
Okuda, T. et al, Molecular Structures and Pharmacological activities of Polyphenols—Oligomeric Hydrolyzable Tannins and Others—Presented at the XVIth International Conference of the Groupe Polyphenols, Lisbon, Portugal, Jul. 13-16, 1992.
Ozanne, et al., Organic Letters, vol. 5 No. 16 pp. 2903-2906.
Pierre. M.C. et al. Tetrahedron Letters 38, (32), 5639-5642 (1997).
Porter, L.J. "Flavans and Proanthocyanidins" from "The Flavonoids" Ed. J.B. Harborne, Chapmen and Hall Ltd., p. 21-62 (1988).
Roux & Ferreira, Fortschritte d. Chemie Org. Naturst., pp. 47-76 (1982).
Roux, D.G. et al, *J. Agric. Food Chem.* 28:216-222 (1980).
Saito, Akiko et al., "Synthetic Studies of Proanthocyanidins. Highly Stereoselective Synthesis of the Catechin Dimer, Procyanidin-B3", Biosci. Biotechnol. Biochem., 66(8), 1764-1767, 2002.
Steenkamp et al, Tetrahedron letters, 26, (25) 3045-3048 (1985).
Steynberg, P.J. et al, Tetrahedron 54:8153-8158 (1998).
Takashi Tanaka et al. Phytochemistry, vol. 53 pp. 311-316 (2000).
Toshima, K., Tatsuta, K., *Chem. Rev.*, 93, 1503-1531 (1993).
Tuckmantel Werner et al., J. Am. Chem. Soc. 1999, 121, 12073-12081.
Weinges, K. et al. *Chem. Ber.* 103, 2344-2349 (1970).
Delcour, et al., "Synthesis of Condensed Tannins. Part 13. The First 2,3-trans-3,4-cis . . . " J. Chem. Soc. Perkin Trans. I (1985) 669-676.
Foo, et al., "Proanthocyanidins From *Lotus corniculatus*" Phytochemistry (1996) 41, No. 2: 617-624.
Kolodziej, "The first 2,3-trans-3,4-cis Procyanidin" Phytochemistry (1985) 24, No. 10: 2460-2462.
Mayer, et al., "Procyanidino-(-)-Epicatechin . . . " Tetrahedron Letters (1996) No. 4: 429-435.
Saito, et al., "Synthetic Studies of Proanthocyanidins. Part 2: Stereoselective gram-scale synthesis . . . " Tetrahedron Letters (2002) 58:7829-7837.
Saito, et al., "Synthetic Studies of Proanthocyanidins. Part 3: Stereoselective 3,4-cis catechin . . . " Tetrahedron Letters (2003) 44:5449-5452.
Viswanadhan et al., "Assessment by Molecular Mechanics of the Preferred Conformations . . . " J. Chem. Soc. Perkin Trans. II (1987) 739-743.

\* cited by examiner

SYNTHESIS OF OLIGOMERIC EPICATECHIN AND CATECHIN-DERIVED PROCYANIDINS

CROSS-REFERENCE TO RELATED APPLICATIONS

This application claims priority to PCT/US03/31375, filed Oct. 2, 2003, which is a continuation in part of Ser. No. 10/658,241 filed Sep. 9, 2003, now U.S. Pat. No. 7,067,679, which is a utility application based on provisional application Ser. No. 60/415,616 filed Oct. 2, 2002.

BACKGROUND OF THE INVENTION

Condensed tannins (proanthocyanidins) are widespread in the plant kingdom, form part of the human diet, and display multiple biological activities that render them significant to health. Procyanidins have attracted a great deal of recent attention in the fields of nutrition, medicine and health due to their wide range of potentially significant biological activities. There is a growing body of evidence suggesting that these compounds act as potent antioxidants in vitro, ex vivo and in vivo and may thus alter the pathophysiology of imbalances or perturbations of free radical and/or oxidatively driven processes in many diseases or directly interfere with many cellular processes. See Nijveldt, R. J. et al., *Am. J. Clin. Nutr.* 2001, 74, 418. Initial observations also have shown that procyanidin-rich fractions extracted from defatted cocoa beans elicited in vitro growth inhibition in several human cancer cell lines. See U.S. Pat. No. 5,554,645 issued Sep. 10, 1996 to L. J. Romanczyk, Jr. et al., the disclosure of which is incorporated by reference.

Isolation, separation, purification, and identification methods have been established for the recovery of a range of procyanidin oligomers for comparative in vitro and in vivo assessment of biological activities, and currently some oligomers can be synthesized using time-consuming methods. For instance, previous attempts to couple monomeric units in free phenolic form using mineral acid as the catalyst in aqueous media have met with limited success. The yields were low, the reactions proceeded with poor selectivity, and the oligomers were difficult to isolate. See Steynberg, P. J., et al., *Tetrahedron*, 1998, 54, 8153–8158. An overview of the shortcomings is set out below.

The benzylated monomer was prepared from the free monomer using benzyl bromide in combination with potassium carbonate ($K_2CO_3$) and dimethyl formamide (DMF). See Kawamoto, H. et al., *Mokuzai Gakkashi*, 1991, 37, 741–747. The yield, however, was only about 40%. In addition, competing C-benzylation leads to a mixture of products, which make isolation of the benzyl-protected target monomer more difficult. Also, partial racemization of (+)-catechin at both the C-2 and C-3 positions was observed (see Pierre, M.-C. et al., *Tetrahedron Letters*, 1997, 38, 5639–5642).

Two primary methods for oxidative functionalization are taught in the literature. See Betts, M. J. et al., *J. Chem. Soc., C,* 1969, 1178 and Steenkamp, J. A., et al., *Tetrahedron Lett.*, 1985, 3045–3048. In the older method, protected (+)-catechin was treated with lead tetraacetate (LTA) in benzene to produce the 4β-acetoxy derivative which was then successfully hydrolyzed to the 3,4-diol. Flavan-3,4-diols are incipient electrophiles in the biomimetic synthesis of procyanidins. The major drawback in the oxidative functionalization of the prochiral benzylic position was a low yield (30–36%) of the acetate during the lead tetraacetate (LTA) oxidation.

The more recent method of oxidatively functionalizing the C-4 position relies on the use of 2,3-dichloro-5,6-dicyano-1,4-benzoquinone (DDQ). In this method, the protected monomer was treated with DDQ in methanol. This allows introduction of a methoxyl group at the C-4 position in a stereoselective manner. The yield was about 40–50%

There are a number of reports on the coupling reaction between monomers and their 3,4-diols in aqueous acid. These methods are unsatisfactory because of low yields, lack of selectivity, and difficulty in the purification from aqueous media. See Kawamoto, H. et al., *J. Wood Chem. Technol.*, 1989, 9, 35–52 who report the titanium tetrachloride ($TiCl_4$) mediated coupling between 4-hydroxy-tetra-O-benzyl-(+)-catechin and 5 equivalents (eq.) of tetra-O-benzyl-(+)-catechin to produce a 3:2 mixture of 4α,8 and 4β,8 catechin dimers. This coupling leads to the 4β,8-dimer together with higher oligomers in yields that decrease with the increasing molecular mass of the oligomer.

Using a 2,3-cis-3,4-trans-flavan-3,4-diol, procyanidins $B_2$ and $B_5$ derivatives were synthesized. The diol was prepared by the acyloxylation of the C-4 benzylic function of a (−)-epicatechin tetramethyl ether with lead tetraacetate in a benzene solution. This oxidative functionalization of the C-4 position of the methyl-protected epicatechin monomer was improved by using 2,3-dichloro-5,6-dicyano-1,4-benzoquinone(DDQ) in methanol to introduce a methoxyl group at the C-4 position. The protected C-4 methoxy monomer was used in the synthesis of 4,8-linked linear procyanidin oligomers up to the trimers. See Steenkamp et al., *Tetrahedron. Lett.* 1985, 26, 3045–3048.

Procyanidin oligomers were prepared using a protected epicatechin or catechin monomer having, as a C-4 substituent, a $C_2$–$C_6$ alkoxy group having a terminal hydroxy group such as a 2-hydroxyethoxy group. The protecting groups used are those that do not deactivate the A ring of the monomer, e.g., benzyl protecting groups. See Kozikowski, A. P. et al. *J. Org. Chem.* 2000, 65, 5371–5381 and U.S. Pat. No. 6,207,842 (issued Mar. 27, 2001 to Romanczyk, L. J. et al.). The C-4 derivatized, protected monomer was coupled with a protected catechin monomer or protected epicatechin monomer to form a protected 4,8-dimer which was then deprotected or used for further coupling with another protected, C-4 derivatized epicatechin monomer to form protected higher 4,8-oligomers. If a 4,6-linkage was desired, the C-8 position of the protected catechin or epicatechin monomer was blocked with a halogen group prior to coupling with the C-4 derivatized, protected epicatechin monomer or oligomer. Higher oligomers having both 4,8- and 4,6-linkages were also prepared. The protected dimers or oligomers were deprotected, and if necessary, deblocked. The coupling was carried out in the presence of a protic acid or a Lewis acid such as titanium tetrachloride ($TiCl_4$). The stereochemical nature of the interflavan bond was confirmed by the synthesis of a specifically protected derivative and its subsequent degradation reference. Unfortunately, titanium tetrachloride-mediated further chain extension of the epicatechin dimer leads to the formation of regioisomers. This is a serious drawback, not only in terms of yield, but also purity. Even though the 4β,8-trimers and 4β,8-tetramers were isolated in pure form, the same cannot automatically be expected for the larger oligomers, for which the number of possible isomers, and thus contaminants, grows rapidly.

One potential way of dealing with this problem is to carefully purify the chain-extended oligomer after each step in order to ensure that all chain-extended oligomers are at least derived from a single isomer of the starting oligomer. However, upon the titanium tetrachloride-mediated chain extension of the protected trimer (2 eq.) with the C-4 derivatized, protected monomer, not only were the protected tetramer, pentamer, and small amounts of higher oligomers formed, but the protected trimer was degraded to the monomer and dimer, which then participated in the chain-extension reaction, giving rise to regioisomeric oligomers such as small amounts of the protected 4β,6:4β,8-trimer. While the reaction conditions (methylene chloride/tetrahydrofuran (9:11), 0° C., 15 min, then room temperature, 140 min) were not optimized, the observation of this deleterious aide reaction warranted a search for a better synthetic approach.

Thus, there is a need for improved methods for synthesizing epicatechin or catechin oligomers, particularly the higher oligomers, and a process for using protected larger epicatechin or catechin oligomers as building blocks for chain extension to even larger oligomers.

SUMMARY OF THE INVENTION

In one embodiment, bis(5,7,3',4'-tetra-O-protected)-epicatechin and/or -catechin (4,8)-dimer and higher (4,8)-oligomers are prepared by coupling a (5,7,3',4'-tetra-O-protected)-epicatechin or -catechin monomer with a 5,7,3',4'-tetra-O-protected-4-(alkoxy)-epicatechin or -catechin monomer in the presence of an acidic clay. The protecting groups used should not deactivate the A ring of the protected monomers or the A ring of the upper unit (i.e., mer) of the protected oligomers. The preferred protecting groups are benzyl groups. A suitable 4-alkoxy group is a $C_2$–$C_6$ alkoxy group having a terminal hydroxy group, preferably 2-hydroxyethoxy. When the monomers are benzyl-protected, the protected epicatechin (4β,8)-dimer is produced in significantly increased yields. Under the same conditions, the benzyl-protected epicatechin (4,8)-trimer, -tetramer, and -pentamer are obtained regioselectively from the next lower 5,7,3',4'-tetra-O-benzyl)epicatechin and/or catechin (4,8)-oligomer. The preferred acidic clay is a montmorillonite clay. The protected monomers and protected oligomers are separated by column chromatography, and then the protecting groups are replaced with hydrogen.

A process is also provided for chain extending a tetra-O-benzyl-protected-epicatechin or -catechin monomers or oligomers with a tetra-O-benzyl-protected-epicatechin or -catechin monomer having a thiol C-4 activating group. The C-4 activated monomer is prepared by reacting a C-4 activated, tetra-O-protected-epicatechin or -catechin monomer (e.g. 5,7,3',4'-tetra-O-benzyl-4-(2-hydroxyethoxy)epicatechin with a thiol derivatizing reagent such an organoaluminum thiolate generated from 2-mercaptobenzothiazole or other heterocyclic thiol, e.g., 2-pyridinethiol, 4-pyridinethiol, or 4-phenyl-1H-tetrazole-5-thiol. Preferably, to avoid the undesired intervention of the C-3 hydroxyl group, this group is protected in both the electrophilic and nucleophilic reaction partners by acetylation. The acetylation is carried out after the tetra-O-benzyl protected monomer is activated by introduction of the 4-thio group. The chain extension is carried out in the presence of dimethy(methythio)sulfonium tetrafluoroborate or preferably silver tetrafluoraborate. Preferably, the silver tetrafluoroborate is dried before the reaction. More preferably the drying is vacuum drying carried out immediately before the reaction. The resulting mixture comprises protected trimers through protected octamers. The protected oligomers are isolated by reverse phase high pressure liquid chromatography. If present, the acetyl protecting group(s) are removed, preferably with aqueous tetra-n-butyl ammonium hydroxide. The benzyl protecting groups are removed by hydrogenolysis, preferably after removal of the acetyl protecting group(s) if such groups are present. With epicatechin, the yields are near-quantitative. The oligomers are characterized as their peracetates.

In another embodiment, chain extension by cross-coupling of two 5,7,3',4'-tetra-O-benzyl-protected-epicatechin or -catechin (4β,8)-oligomers each having a C-4 thio activating group (e.g., C-4-(2-benzlothiazolyl)thio) is carried out in the presence of silver tetrafluoroborate.

An improved process is also provided for preparing a 5,7,3',4'-tetra-O-benzyl-4-alkoxy-8-bromo-epicatechin or -catechin monomer. In the prior art four step process for preparing the C-8 blocked, C-4 alkoxy monomers the yield was about 51%. The steps included (i) the C-4 activation of 5,7,3',4'-tetra-O-benzyl-epicatechin by reaction with ethylene glycol in the presence of 2,3-dichloro-5,6-dicyano-1,4-benzoquinone(DDQ) (63% yield), (ii) protection of the 3-hydroxyl position of the C-4-(2-hydroxyethoxy)-5,7,3',4'-tetra-O-benzylepicatechin by the introduction of a tert-butyldimethylsilyl (TBDMS) group by reaction with tert-butyldimethylsilyl chloride in imidazole in the presence of 4-dimethyl-aminopyridine (DMAP) (88% yield), (iii) introduction of an 8-bromo group by reaction with N-bromosuccinimide at −40° C. in methylene chloride (100%), and (iv) removal of the TBDMS group by reaction with tetrabutyl ammonium fluoride (TBAF) in tetrahydrofuran (92%). In the improved two step processes 5,7,3',4'-tetra-O-benzyl-epicatechin or -catechin is (i) activated by reaction with ethylene glycol in the presence of DDQ and (ii) blocked by bromination with N-bromosuccinimide or (i) 5,7,3',4'-(tetra-O-benzyl)-epicatechin or -catechin is blocked by bromination and then (ii) activated. The overall yield for the two step process is about 63% when the monomer is epicatechin and the activation is done first and about 67% when the monomer is epicatechin and the blocking is done first.

The synthetic procyanidin oligomers are identical to the procyanidin oligomers isolated from cocoa bean extracts by normal-phase HPLC. The regio- and stereochemistry of the interflavan linkages has been established by partial thiolysis (see Hör, M. et al., *Phytochemistry* 1996, 42, 109). For the tetramer the upper interflavan linkage is 4β,8 and the lower portion of the molecule is identical to the trimer which has also been subjected to partial thiolysis with both linkages being identified as 4β,8 (see Hör et al.). Since in the course of the present chain extension process the first three interflavan linkages formed are exclusively 4β,8 linkages, the same must be true for the additional interflavan linkages present in the higher oligomers.

When tested in several breast cancer cell lines, both the synthetic and natural procyanidin pentamer, and to a lesser extent the tetramer, inhibited cell growth. Using the MDA MB-231 cell line, it was established that this outcome is based on the induction of cell cycle arrest in the $G_0/G_1$ phase. Subsequent cell death is more likely necrotic rather than apoptotic. Control experiments demonstrate that the procyanidin itself, rather than hydrogen peroxide, is the causative agent.

DESCRIPTION OF THE PREFERRED EMBODIMENTS

A. Chain Extension of Protected Eipicatechin Dimers and Trimers Mediated by Acidic Clay Chain extension of 5,7,3',4'-tetra-O-benzylepicatechin and 5,7,3',4'-tetra-O-benzyl catechin mediated by an acidic clay such as Montmorillonite clay (e.g., Bentonite K-10) results in the almost exclusive formation of the protected (4β,8)-dimers. When the protected monomer was the epicatechin, the isolated yield was 90% together with small amounts of the protected (4β,8)$_2$-trimer, and no 4,6-linked oligomers are observed. The surprisingly high reactivity differential under these conditions between the monomer and the dimer allows most of the dimer to survive without entering into further chain extension. Reaction of bis(5,7,3',4'-tetra-O-benzyl)epicatechin (4β,8)-dimer with 5,7,3',4'-tetra-O-benzylepicatechin activated at the C-4 position with a 2-hydroxyethoxy group yields 40% of the (4β,8)$_2$-trimer together with 13% of the (4β,8)$_3$-tetramer by this chain extension protocol. The cleanness of this reaction permits, for the first time, at least a partial separation of the monomer from the dimer, and even of the dimer from the trimer, by column chromatography. This significantly reduces the amount of material that needs to be put through HPLC purification.

B. Chain Extension of 5,7,3',4'-Protected or 3,5,7,3',4'-Protected Epicatechin or Catechin Monomers Having A C-4 Thio Group In an alternative chain extension, a 5,7,3',4'-protected-epicatechin or -catechin is activated at the C-4 position with a thiol group such as 2-(benzothiazolyl)thio. The chain extension is mediated by silver tetrafluoroborate. The reagent used to introduce the 2-(benzothiazolyl)thio group at the C-4 position of an epicatechin or a catechin monomer is 2-mercaptobenzothiazole which is a non-volatile, odorless heterocyclic thiol. For this chain extension, C-4 derivatized-C-5,7,3',4'-benzyl-protected monomers, rather than the unprotected monomers, are preferred because they are easier to handle, more stable, and more accessible than the unprotected, C-4 derivatized monomers. The thio group can also be introduced by reaction with 2-pyridinethiol, 4-pyridinethiol, or 1-phenyl-1H-tetrazole-5-thiol.

The monomer having the 2-(benzothiazoyl)thio activating group is prepared by reacting a protected epicatechin or catechin having a 2-hydroxyethoxy group at the C-4 position with an organoaluminum thiolate prepared in situ from 2-mercaptobenzothiazole and trimethylaluminum. See Dzhemilev U. M. et al., *Izv. Akad. Nauk SSSR, Ser. Khim.*, 1988, 2645. The resulting 4-thioether is a mixture of two stereoisomers which are isolated by fractional crystallization and column chromatography. Only the major stereoisomer is used for the subsequent coupling but the minor stereoisomer can be used as well.

The chain extension is effected by adding silver tetrafluoride borate (AgBF$_4$) to a solution of 5,7,3',4'-tetra-O-benzylepicatechin or 5,7,3',4'-tetra-O-benzylcatechin and the major stereoisomer. This results in the formation of a protected procyanidin (4β,8)-dimer and (4β,8)$_2$-trimer. After normal-phase HPLC separation, the protected dimer, trimer, and monomer are recovered. Further separation by reverse-phase HPLC yields, as a by-product, a protected 3-O-4 dimer. To avoid the undesired reaction of the 3-hydroxyl group in this chain extension process, the 3-hydroxyl group is protected by acetylation of both the benzyl-protected monomer and the benzyl-protected dimer. The yields are near-quantitative. When a solution of silver tetrafluoroborate is added to a solution of the acetyl- and benzyl-protected dimer and acetyl- and benzyl-protected monomer, the expected acetyl- and benzyl-protected trimer and tetramer are formed, but only in low yields. The reason that the chain extension proceeds so slowly is that adventitious water successfully competes with the flavanoid nucleophile, with the major product of the coupling being the 4-hydroxy monomer 3-O-acetyl-5,7,3',4'-tetra-O-benzyl-acetyl-4-hydroxyepicatechin. In addition, small amounts of the 4-hydroxy dimer, 3-O-acetyl-5,7,3',4'-tetra-O-benzyl-4β,8-(3-O-acetyl-5,7,3',4'-tetra-O-benzyl-4-hydroxyepicatechin), are also isolated, indicating self-condensation of the thioether followed by either chain extension or hydrolysis.

In an attempt to improve the yield, the protected dimer and protected monomer are dried by stirring with powdered molecular sieves prior to the addition of the silver tetrafluoroborate. The yield, however, remained unchanged. If the AgBF$_4$ is initially dried with molecular sieves, and the remaining reactants are added, no reaction takes place. Vacuum drying the silver tetrafluoroborate immediately before the coupling solves the problem by reducing the hydrolysis of 3-O-acetyl-4-[(2-benzothiazolyl)thio]-5,7,3',4'-tetra-O-benzlepicatechin to an acceptable level.

Using dry silver tetrafluoroborate with a protected monomer to protected dimer molar ratio of 1:2.5, a series of protected oligomers spanning from the trimer, tris(3-O-acetyl-5,7,3',4'-tetra-O-benzyl)epicatechin (4β,8)$_2$-trimer to the octamer octakis(3-O-acetyl-5,7,3',4'-tetra-O-benzyl)epicatechin (4β,8)$_7$-octamer, can be isolated in a combined yield of 91%. The reaction is exceptionally clean, and no 4,6-oligomers are observed.

Similar results are obtained in the coupling of the C-4 derivatized, benzyl- and acetyl-protected monomer with the benzyl- and acetyl-protected trimer and tetramer. From these reactions, oligomers up to the protected undecamer can be isolated by reverse-phase HPLC if ethyl acetate (a nonpolar solvent) is admixed with the acetonitrile in the final step of the gradient. The use of the ethyl acetate permits recovery of the highly retained higher oligomers; however, it also elutes significant amounts of aliphatic impurities which subsequently have to be removed by additional HPLC steps, thus reducing the total product recovery.

All of the protected oligomers (i.e., the benzyl ether-acetates) up to the nonamer were deacetylated in near-quantitative yield with 40% aqueous tetra-n-butylanunonium hydroxide in tetrahydrofuran. This base is used because of its good solubility in the relatively nonpolar reaction medium that is required by the lipophilicity of the starting materials. The $^1$H NMR spectra of the resulting benzyl-ethers displayed signals of two major rotamers together with trace amounts of additional rotamers that increase as the oligomeric chain grows. It is believed that these minor components are rotamers rather than regioisomers because similar signals are absent from the spectra of the precursor acetates. Samples of the benzyl ethers prepared in CDCl$_3$ exhibit well-resolved, characteristic signals for the hydroxyl (OH) protons in the δ 1.8–1.1 region.

The benzyl ethers (trimer through the octamers) are deprotected by hydrogenolysis over Pearlman's catalyst to form the unprotected oligomers. Preferably, this deprotection is carried out in bicarbonate-washed glassware, as partial fragmentation to lower oligomers is occasionally observed without this precaution, quite probably as a consequence of the acidity of the glass surface of the reaction flask. To obtain a readily soluble procyanidin, it is necessary, as similarly reported by others, to dilute the filtered solution of the crude product with water, evaporate only partially so as to remove most of the organic solvents, and lyophilize the residual solution. If the crude solutions are directly evaporated to dryness, partially insoluble materials result, indicating that some decomposition has occurred. Combustion analyses shows that the lyophilized products contain 1.3–2 equivalents of water per epicatechin moiety.

Comparison by normal phase HPLC analysis of epicatechin (4β,8)$_2$-trimer, epicatechin (4β,8)$_3$-tetramer, and epicatechin (4β,8)$_4$-pentamer was made against the natural trimer, tetramer, and pentamer purified from *Theobroma cacao*. Purities ranging from 94% to 96% were observed for the synthetic procyanidins which were 2–4% higher than those for the naturally-derived oligomeric procyanidins. The $t_R$'s of the synthetic procyanidins match those observed for the natural oligomers, thus confirming the epicatechin 4β,8 regio- and stereochemistry in the natural cocoa procyanidins. All of the natural procyanidins purified from cocoa show impurity peaks preceding and following the main peak, with the tetramer and pentamer showing more impurity peaks. Scanning these regions by HPLC/MS reveals no change in the [M]$^+$ or [M+Na]$^+$ ions indicating that these minor impurities are isomers of the major oligomers. These minor impurities may contribute to in vitro and in vivo activities reported in the literature and potentially confound structure-activity relationships based only on natural oligomers. Hence, as a precaution, both natural and synthetic procyanidins are therefore used in the biological assays reported in the following examples.

The nature of the impurities and of the side reaction(s) leading to them has not been established but several trace impurities are present rather than a single major one. This is less than ideal; however, comparison of reported optical rotations, for example, of the free (4β,8)-dimer or the tetramer reveals large variations that cannot merely be the consequence of differential degrees of hydration, but appear to indicate the presence of unknown impurities in some of these samples as well.

Since free polyphenols are inherently poorly amenable to purification because of their oxygen and acid sensitivity (acid being required as a solvent additive to reduce peak tailing during HPLC), and their NMR spectra are anyway uncharacteristic because of severe line broadening, these compounds are characterized as their peracetates. The $^1$H NMR spectra of the peracetates exhibit sharp signals for two rotamers (in a 2;1 ratio for the trimer and in a 3:2 ratio for all higher homologs) and are, up to the heptamer or octamer, quite suitable for compound identification, since the acetate region serves as a useful "fingerprint". As the oligomeric chain grows, the chemical shift differences between analogous protons of epicatechin units in the inner position of the chain become eventually insufficient at 300 MHz, resulting in the growth of uncharacteristic signal clusters without the appearance of well-separated new signals. These spectra can be useful for future reference. 13C NMR spectra are available for oligomers up to the hexamer, beyond which insufficient amounts of material are available. The $^1$H NMR spectra are of the trimer and tetramer in good agreement with published spectra. See Hör, M. et al., *Phytochemistry*, 1996, 42, for the trimer and tetramer and Sticher, O. F., *Chromatogr. A*, 1999, 835, 59 for the trimer. In the case of the tetramer, partial thiolysis (see Hör et al.) establishes (4β,8)-regio- and -stereochemistry for the "upper" interflavan linkage, whereas the "lower" portion of the molecule is identical with the trimer. This compound, in turn, has also been subjected to partial thiolysis, and both interflavan linkages have been identified as (4β,8) (see Hör et al.). Since, therefore, in the chain extension process the first three interflavan linkages formed are exclusively of the 4β,8 type, the same must be true for the additional interflavan linkages present in the larger oligomers.

C. Cross Coupling of 3,5,7,3',4'-Protected Monomers Having C-4 (2-Benzothiazolyl)thio Groups and of a 3,5,7,3', 4'Protected Oligomer Having a C-4 (2-Benzothiazolyl)thio and a 3,5,7,3',4'-Protected Oligomer 5,7,3',4'-Tetra-O-benzylepicatechin monomers having 2-(benzothiazolyl)thio groups at the C-4 position self-condensed in the presence of silver tetrafluoraborate to yield a fairly complex mixture from which small amounts of the benzyl-protected, 4-[(2-benzothiazolyl)thio]-dimer, -trimer, and presumably-tetramer can be isolated. Also isolated are the rearranged benzyl-protected monomer and dimer where the group at the C-4 position is connected to the nitrogen rather than the sulfur of the thiazoyl ring. The migration of this moiety from sulfur to nitrogen is confirmed for the monomer by the observation of a $^{13}$C NMR signal at δ 190.3 assignable to the thiocarbonyl carbon atom. The complexity of the above reaction mixture is in part due to the formation of 4-O-3-linked oligomers similar to 5,7,3',4'-tetra-O-benzyl epicatechin 4-O-3-(5,7,3,4-tetra-O-benzylepicatechin. AgBF$_4$-induced self-condensation of 3-O-acetyl-4-[(2-benzothiazolyl)thio]-5,7,3',4'-tetra-O-benzylepicatechin results in low yields of the 4-[(2-benzothiazolyl)thio]-substituted oligomers, i.e., dimer, trimer and tetramer. Together with these products, and in considerable quantities because of the small reaction scale, the 4-hydroxy by-products are also formed. The by-products are 3-O-acetyl-5,7,3',4'-tetra-O-benzylepicatechin-(4β,8)-(3-O-acetyl-5,7,3',4'-tetra-O-benzyl-4-hydroxyepicatechin, 3-O-acetyl-5,7,3',4'-tetra-O-benzylepicatechin-(4β,8)-(3-O-acetyl-5,7,3',4'-tetra-O-benzylepicatechin)-(4β,8)-(3-O-acetyl-5,7,3',4'-tetra-O-benzyl-4-hydroxyepicatechin, and 3-O-acetyl-5,7,3',4'-tetra-O-benzylepicatechin-bis[(4β,8) -(3-O-acetyl-5,7,3',4'-tetra-O-benzylepicatechin)]-(4β,8)-(3-O-acetyl-5,7,3',4'-O-benzyl-4-hydroxyepicatechin).

Reaction of [3-O-acetyl-5,7,3',4'-tetra-O-benzylepicatechin-(4β,8)-[3-O-acetyl-4-(2-benzothiazolyl)thio)-5,7,3', 4'-tetra-O-benzylepicatechin] with tetrakis (3-O-acetyl-5,7, 3',4'-tetra-O-benzylepicatechin (4β,8)$_3$-tetramer in the present of silver tetrafluoroborate resulted in the formation of the expected hexamer, i.e., hexakis (3-O-acetyl-5,7,3',4'-tetra-O-benzylepicatechin (4β,8)$_5$-hexamer in 12% yield together with the by-products octakis (3-O-acetyl-5,7,3',4'-tetra-O-benzylepicatechin 4β,8)$_7$-octamer, 3-O-acetyl-5,7, 3',4'-tetra-O-benzylepicatechin)-4β,8-(3-O-acetyl-5,7,3',4'-tetra-O-benzyl-4-hydroxyepicatechin), and 3-O-acetyl-5,7, 3',4'-tetra-O-benzylepicatechin 4β,8-(3-O-acetyl-5,7,3',4'-tetra-O-benzlepicatechin)-4β,8(3-O-acetyl-5,7,3',4'-tetra-O-benzyl-4-hydroxyepicatechin).

Thus, chain elongation can be performed in increments of two flavanol units. This procedure should be of use for the chain-extension of the larger protected epicatechin oligomers as these compounds far exceed the monomeric 5,7,3', 4'-protected, C-4 derivatized building blocks in value.

D. Improved Process for Preparing 5,7,3',4'-tetra-O-benzyl-epicatechin and -catechin Monomers having a Bromo Blocking Group at the C-8 Position The C-4 position of a 5,7,3',4'-tetra-O-benzyl-epicatechin or -catechin monomer is activated by the introduction of an alkoxy group (e.g., 2-hydroxyethoxy) and the C-8 position is blocked with a bromo group. The activating and blocking step can be carried out in any sequence with the yield varying from about 63% to 67%. The activation is carried by reacting the protected monomer or the blocked protected monomer. Ethylene glycol in the presence of DDQ. The protection is carried out by reacting the protected monomer or activated, protected monomer with N-bromosuccinimide at −40° C. in methylene chloride.

E. Preparation of Procyanidin (4,8)-Dimer Digallates

Epicatechin- and/or catechin-(4,8) dimer digallates are prepared by esterifying octa-O-protected (4,8) dimers with hydroxy-protected gallic acid, preferably bydroxy-galloyl acid chloride. The preferred protecting groups for both the dimer and the acid or acid halide are benzyl groups. The dimer digallates which can be prepared include epicatechin-(4β,8)-epicatechin digallate, epicatechin-(4β,8)-catechin -(4α,8)-catechin digallate, catechin-(4β,8)-catechin digallate, catechin-(4α,8)-epicatechin digallate, and catechin-(4β,8)-epicatechin digallate.

A tetra-O-protected (4,8)-epicatechin and/or -catechin dimer (e.g., 5,7,3',4'-tetra-O-benzylepicatechin) is esterified with tri-O-benzyl galloyl halide. Tri-O-benzyl gallic acid can be converted in situ into a halide, e.g., chloride. The esterification is carried out in pyridine solution in the presence of 4-dimethylaminopyridine (DMAP). Hydrogenolysis over 20% Pd $(OH)_2$/C gives the deprotected bisgallate. When the dimer is an epicatechin-(4β,8)-epicatechin, the deprotected bisgallate is recovered in 90% yield as a hydrate without need for chromatographic purification (5.3 equiv. of water per bisgallate molecule).

The preparation of epicatechin-(4β,8)-epicatechin bisgallate is disclosed in "Studies in Polyphenol Chemistry and Bioactivity. 1. Preparation of Building Blocks from (+)-catechin. Procyanidin Formation. Synthesis of the Cancer Cell Growth Inhibitor, 3-O-Galloyl-(2R,3R)-epicatechin-(4β,8)-[3-O-galloyl-(2R,3R)-epicatechin] by W. Tückmantel et al., *J. Am. Chem. Soc.*, 1999, 121, 12073–12081. The preparation of gallic acid esters of epicatechin-(4α,8)-epicatechin bisgallate is disclosed in "Studies in Polyphenol Chemistry and Biology. 3. Stereocontrolled Synthesis of Epicatechin-4α,8-epicatechin, an Unnatural Isomer of the β-Type Procyanidin, Alan P. Kozikowski et al., *J. Org. Chem.*, 2001, 66, 1287–1295.

Reagents, Test Procedures, and Analytical Procedures
Reagents

Pearlman's catalyst (20% Pd$(OH)_2$/C) was obtained from Aldrich and contained up to 50% $H_2O$. Bentonite K-10 was purchased from Acros. For other chemicals, see Tückmantel, W. et al., *J. Am. Chem. Soc.*, 1999, 121, 12073.

Acetylation

Since the free procyanidins are poorly amenable to purification because of their oxygen and acid sensitivity and their NMR spectra are uncharacteristic because of severe line broadening, these compounds are characterized as their peracetates. The $H^1$ NMR spectra of the peracetates exhibit sharp signals for two rotameters (in a 2:1 ratio for the trimer and in a 3:2 ratio for all higher oligomers). The spectra up to the octamer are quite suitable for compound identification. The acetate region serves as a useful "fingerprint". 13C NMR spectra have been acquired for oligomers up to the hexamer.

The $^1H$ NMR spectra for the trimer and tetramer are in good agreement with those published.

Spectra $^1H$ and $^{13}C$ NMR spectra were acquired at nominal frequencies of 300 and 75 MHz, respectively, in $CDCl_3$ unless specified otherwise. $^1H$ NMR spectra are referenced to internal TMS; $^{13}C$ NMR spectra to internal TMS if so marked or otherwise to the $CDCl_3$ signal (δ 77.00). Combustion analyses were carried out by Micro-Analysis, Inc. (Wilmington, Del.).

Column Chromatography

Column chromatography (CC) was carried out on Merck silica gel 60 (No. 7734-7), particle size 63–200 μm. TLC: Merck silica gel 60 $F_{254}$ (No. 7734-7), layer thickness 250 μm; visualization by UV light or with alkaline $KMnO_4$ solution.

High Pressure Liquid Chromatopraphic (HPLC) Analysis of Procyanidins

Chromatographic analyses of free procyanidin oligomers were performed on a HP 1100 HPLC system (Hewlett Packard, Palo Alto, Calif.) equipped with an autoinjector, quaternary HPLC pump, column heater, diode array detector, fluorescence detector, and HP ChemStation for data collection and sample manipulation. Normal phase separations were performed on a 250×4.6 mm Phenomenex (Torrance, Calif.) 5 μm Prodigy column. The detector was a fluorescence detector operating at $\lambda_{ex}$=276 nm and $\lambda_{em}$=316 nm. The ternary mobile phase consisted of (A) dichloromethane, (B) methanol and (C) acetic acid:water (1:1 v/v). Separations were effected by a series of linear gradients of B into A with a constant 4% C at a flow rate of 1 mL/minutes as follows: 0–30 minutes, 14.0–28.4% B in A; 30–50 minutes, 28.4–38.0% B in A; 50–51 minutes, 38.0–86.0% B in A; 51–56 minutes, 86.0% B in A isocratic.

Other HPLC: columns: column A, Hewlett-Packard RP-8, 200×4.6 mm, at 1.0 mL/min; column B, Waters μBondapak $C_{18}$, 300×7.8 mm, at 2.8 mL/min; column C, Waters μBondapak $C_{18}$, 300×19 mm; column D, Waters μBondapak $C_{18}$, 300×30 mm, at 42 mL/min; column E, Whatman Partisil 10, 500×9.4 mm, at 5.0 mL/min; column F, Whatman Partisil 10, 500×22 mm, at 26 mL/min. Detection was by UV absorption at 280 nm. Retention times varied substantially depending on column history and other subtle circumstances. They are quoted solely for orientation and should not be employed for product identification without comparison to an authentic reference sample. See examples for further details.

High Pressure Liquid Chromatgraphic/Mass Spectra (HPLC/MS) Analysis of Procyanidins HPLC/MS analyses of natural and synthetic procyanidins were performed on an HPLC system (as described above) which was interfaced to an HP Series 1100 mass selective detector (Model G1946A) equipped with an API-ES ionization chamber. Ionization reagents were added via a tee in the eluent stream just prior to the mass spectrometer. Conditions for analysis in the positive ion mode included the introduction of 0.05 M sodium chloride at a flow rate of 0.05 mL/minutes to assist ionization, a capillary voltage of 3.5 kV, a fragmentor voltage of 100 V, a nebulizing pressure of 25 psig, and a drying gas temperature of 350° C. Scans were performed over a mass range of m/z 100–3000 at 1.96 s per cycle.

Cell Lines

The human breast cancer cell lines MCF-7, SKBR-3, MDA 435, and MDA MB-231 were obtained from the Lombardi Cancer Center Cell Culture Core Facility at Georgetown University Medical Center. The MDA MB-231 cell line was P53 defective, ER negative, and constitutively expressed K-ras. Cells were cultured in T-75s in IMEM medium (BioFluids Inc.) supplemented with 10% FBS (Gibco BRL Life Technologies) in a humidified 5% $CO_2$ atmosphere at 37° C.

Cytotoxicity Assay

Cytotoxicity assays were performed on several human breast cancer cell lines treated with test compounds in a 96 well microtiter plate format using the microculture tetrazolium assay[28] modified for use with crystal violet rather than MTT. Briefly, 1–2×10³ cells were added per well and allowed to culture in a humidified, 5% $CO_2$ atmosphere until they reached approximately 50% confluence. Sterile filtered test compounds were added at various concentrations, and the plates were allowed to culture for an additional 12–36 hours. The growth medium was then removed, and each well was washed twice with 200 μL each of pH 7.4 PBS. After washing, 50 µL of filtered crystal violet solution (2.5 g/125 mL of methanol+375 mL of H₂O) was added. At the end of 5 minutes, the crystal violet was removed, and the plate was washed three times with water. Plates were allowed to dry, and the crystal violet stained cells were resolubilized in 100 µL of 0.1 M sodium citrate in ethanol/water (1:1, v/v). At the end of 1 hour, the plates were scanned at 570 nm (ref. 405 nm) with a Molecular Devices Corporation microtiter plate reader, and the data was recorded with the SOFTMAX software program. The average of 3 readings was taken for each blank, control, vehicle, and test concentration for statistical data manipulation.

Flow Cytometry

MDA MB-231 cells were cultured as described above until they reach approximately 50% confluence. Sterile filtered test compounds or catalase (Sigma #C9322) adjusted to 100 U/mL or heat inactivated catalase (solution immersed in boiling water for 15 min) or hydrogen peroxide ($H_2O_2$) was then added, and the cells were allowed to culture for an additional 24 h. The cells were then trypsinized and counted, and $1.5 \times 10^6$ cells were taken for cell cycle analysis by the Vindelov method. See Vindelov, L. et al., "A Detergent Trypsin Method for the Preparation of Nuclei for Flow Cytometric DNA Analysis", *Cytometry*, 1983, 3, 323–327. Analyses were performed by the Lombardi Cancer Center Flow Cytometry Core Facility at Georgetown University Medical Center.

Annexin V-FITC

The annexin V-FITC assay was performed on procyanidin-treated MDA MB-231 cells using the TACS™ Annexin V-FITC kit (Trevigen Inc.) according to the manufacturer's procedure.

EXAMPLES

Example 1

Preparation of Tetra-O-Protected, C-4Activated Monomers

Part A—Preparation of 5,7,3',4'-Tetra-O-benzyl-4-(2-hydroxyethoxy)epicatechin

To a solution of 21.5 g (33.0 mmol) of 5,7,3',4'-tetra-O-benzylepicatechin in 220 mL of anhydrous methylene chloride ($CH_2Cl_2$) was added at room temperature 11.0 mL (198 mmol) of ethylene glycol and then all at once with good stirring 15.0 g (66 mmol) of 2,3-dichloro-5,6-dicyano-1,4-benzoquinone(DDQ) was added. After 110 minutes of vigorous stirring at room temperature under a calcium chloride ($CaCl_2$) tube, a solution of 8.5 g (69.5 mmol) of 4-(dimethylamino)pyridine (DMAP) in 50 mL of anhydrous methylene chloride was added whereupon a copious dark precipitate appeared. After another 10 minutes of stirring at room temperature, the mixture was filtered over a coarse glass frit, the precipitate was washed with 50 mL of methylene chloride, and the solution was evaporated to near dryness. The residue was filtered over silica gel (17×9 cm) with ethyl acetate/hexane 1:1, and all product-containing fractions were pooled. After evaporation to approximately 75 mL, crystals began to appear (seeding may be necessary). An equal volume of hexane was added, and crystallization was allowed to proceed at room temperature overnight. Suction filtration, washing twice with 25 mL of ethyl acetate/hexane (1:2), and drying in vacuo (initially at room temperature, then at 40° C.) furnished 10.6 g (45%) of 5,7,3',4'-tetra-O-benzyl-4-(2-hydroxyethoxy)epicatechin as an off-white solid. It was analyzed by HPLC and found to be 97% pure AKA acetanitrile (column B; 0–20 minutes 50 to 100% methylcyanide ($CH_3CN$) in $H_2O$, then $CH_3CN$; $t_R$ 17.9 min). Additional product was obtained from the mother liquor by column chromatography on silica ($SiO_2$) (33×5 cm) and elution with ethyl acetate/hexane (1:2) (forerun), then 2:3 (product). After evaporation, the resulting amber glass (1.0 g, purity 69%) was crystallized twice from ethyl acetate/hexane to yield another 0.5 g (2%) of 5,7,3',4'-tetra-O-benzyl-4-(2-hydroxyethoxy)epicatechin (purity 98%).

Part B—Preparation of 5,7,3',4'-tetra-O-benzyl-4-(2-hydroxyethoxy)catechin

Using the procedure described above the 5,7,3',4'-tetra-O-benzyl-4-(2-hydroxyethoxy)catechin was prepared.

Example 2

Condensation of Tetra-O-Protected Catechin or Epicatechin Monomers with Tetra-O-Protected, C-4 Activated Catechin or Epicatechin Monomers Catalyzed by Acidic Clay Part A—Condensation of 5,7,3',4'-Tetra-O-benzylepicatechin with 5,7,3',4'-Tetra-O-benzyl-4-(2-hydroxyethoxy)epicatechin To a solution/suspension of 9.26 g (14.2 mmol, 4 equiv.) of 5,7,3',4'-tetra-O-benzyl-epicatechin and 5.0 g of Bentonite K-10 clay in 115 mL of anhydrous methylene chloride ($CH_2Cl_2$) was added, with ice cooling, stirring and exclusion of moisture, within 2.5 hours 2.53 g (3.56 mmol) of 5,7,3',4'-tetra-O-benzyl-4-(2-hydroxyethoxy)epicatechin in 35 mL of anhydrous methylene chloride. The bath temperature rose to +6° C. at the end of the addition. Stirring in the bath was continued for 1 hour, during which time the temperature rose to +12° C. The clay was filtered off with suction over celite, and the solids were washed two times with 50 mL of methylene chloride. Twenty mL of toluene was added, and the solution was evaporated to a small volume. The residue was chromatographed on silica gel (60×5 cm) with ethyl acetate/chloroform/hexane (1:14:14). Initially, 5.95 g of unreacted 5,7,3',4'-tetra-O-benzlepicatechin was eluted, followed by 4.01 g of protected monomer/protected dimer mixed fractions and 1.15 g of pure (98% by HPLC) bis(5,7,3',4'-tetra-O-benzylepicatechin (4β,8)-dimer. The last traces of the dimer together with the protected trimer were eluted as a mixed fraction (0.27 g) with a solvent ratio of 1:7:7.

The mixed fractions were each dissolved in methyl cyanide ($CH_3CN$) and separated by preparative HPLC (column D; 0–30 minutes, 80 to 100% ($CH_3CN$) in $H_2O$, then $CH_3CN$; the retention times for the protected dimer and protected trimer were 23.3 and 30.1 minutes, respectively. After combination of the appropriate fractions, evaporation, and drying in vacuo, the following yields were obtained: 5,7,3',4'-tetra-O-benzylepicatechin, 6.89 g (74% recovery); bis(5,7,3',4'-tetra-O-benzyl)epicatechin (4β,8)-dimer, 4.26 g (92%); tris(5,7,3',4'-tetra-O-benzyl)epicatechin (4β,8)₂-trimer 74 mg (2%). Bis-(5,7,3',4'-tetra-O-benzyl)-epicatechin (4β,8)-dimer. $^{13}C$ NMR (CDCl₃, TMS) δ 158.34, 158.07, 157.91, 157.07, 156.83, 156.56, 156.49, 155.89, 155.53, 155.07, 154.44, 152.83, 149.17, 149.01, 148.92, 148.66, 148.60, 148.40, 148.18, 137.40, 137.38, 137.30, 137.28, 137.22, 137.17, 137.01, 136.97, 132.61, 132.43, 131.18, 131.14, 128.6–126.6, 119.96, 119.79, 118.79, 118.65, 115.02, 114.89, 114.35, 114.05, 113.52, 112.93, 112.46, 111.58, 111.17, 104.45, 102.29, 101.76, 94.34, 93.96, 93.33, 93.15, 92.93, 91.52, 78.84, 78.07, 75.63, 72.41, 72.14, 71.48, 71.35, 71.22, 70.81, 70.48, 69.92, 69.86, 69.78, 69.47, 69.05, 66.50, 65.15, 35.90, 35.78, 28.74, 28.61. Other data have been published (see Part 1: Tückmantel, W. et al. *J. Am. Chem. Soc.*, 1999, 121, 12073).

In another run (3.17 mmol of 5,7,3',4'-tetra-O-benzyl-4-(2-hydroxyethoxy)-epicatechin), an essentially complete separation of protected monomer and protected dimer and of protected dimer and protected trimer was achieved during column chromatography, with only the protected trimer and the very dilute tail of the protected dimer requiring purification by HPLC. The following yields were obtained: 5,7,3',4'-tetra-O-benzylepicatechin, 6.20 g (75% recovery); bis(5,7,3',4'-tetra-O-benzyl)epicatechin (4β,8)-dimer, 3.63 g (88%); and tris(5,7,3',4'-tetra-O-benzyl)epicatechin (4β,8)$_2$-trimer, 0.15 g (5%).

Part B—Condensation of 5,7,3',4'-Tetra-O-benzylcatechin with 5,7,3',4'-Tetra-O-benzyl-4-(2-hydroxyethoxy) epicatechin Using the procedure described above, a protected epicatechin-(4β,8)-protected catechin dimer was prepared. The purity ranged from 89–98%.

Part C—Condensation of 5,7,3',4'-Tetra-O-benzylcatechin with 5,7,3',4'-Tetra-O-benzyl-4-(2-hydroxyethoxy) protected catechin Using the procedure described above, a protected catechin-(4β,8)-protected catechin dimer was prepared. The purity ranged from 93–98%.

Part D—Condensation of 5,7,3',4'-Tetra-O-benzylcatechin with 5,7,3',4'-Tetra-O-benzyl-4-(2-hydroxyethoxy) protected catechin Using the procedure described above, a protected catechin-(4α,8)-protected catechin dimer was prepared. The purity ranged from 97–98%.

Part E—Condensation of (5,7,3',4'-tetra-O-benzyl)catechin with (5,7,3',4'-tetra-O-benzyl)-4-(2-hydroxyethoxy) catechin Using the procedure described above, a protected catechin-(4β,8)-protected epicatechin dimer can be prepared by reacting (5,7,3',4'-tetra-O-benzyl)-epicatechin and (5,7,3',4'-tetra-O-benzyl-4-(2-hydroxyethoxy)-catechin.

Part F—Condensation of (5,7,3',4'-tetra-O-benzyl)catechin with 5,7,3',4'-(tetra-O-benzyl)-4-(2-hydroxyethoxy) epicatechin Using the procedure described above, a protected catechin-(4α,8)-protected epicatechin dimer can be prepared by the condensation of 5,7,3',4'-tetra-O-benzyl-epicatechin with (5,7,3',4'-tetra-O-benzyl)-4-(2-hydroxyethoxy)catechin.

Example 3

Condensation of Bis(5,7,3',4'-tetra-O-benzyl)epicatechin (4β,8)-Dimer with 5,7,3',4'-Tetra-O-benzyl-4-(2-hydroxyethoxy)epicatechin Catalyzed by Acidic Clay To a solution/suspension of 5.60 g (4.31 mmol, 3 equiv.) of bis(5,7,3',4'-tetra-O-benzyl)epicatechin (4β,8)-dimer and 2.04 g of Bentonite K-10 clay in 45 mL of anhydrous methylene chloride (CH$_2$Cl$_2$) was added, with ice cooling, stirring and exclusion of moisture, within 110 minutes 1.02 g (1.44 mmol) of 5,7,3',4'-tetra-O-benzyl-4-(2-hydroxyethoxy)-epicatechin in 15 mL of anhydrous methylene chloride (CH$_2$Cl$_2$). The bath temperature rose to +6° C. at the end of the addition. Stirring in the bath was continued for 1 hour, during which time the temperature rose to +12° C. The clay was filtered off with suction over celite, and the solids were washed four times with 25 mL each of ethyl acetate. The combined solutions were evaporated. Attempted separation by column chromatography on silica gel (56×5 cm) with ethyl acetate/hexane/chloroform (1:10:10) failed to separate the dimer and the trimer. Subsequent elution with a solvent ratio of 1:7:7 gave 0.50 g of a fraction consisting mostly of tetramer together with residual trimer. The dimer/trimer fraction was again subjected to column chromatography on silica gel (55×5 cm), this time starting with ethyl acetate/chloroform/hexane 1:14:14. After elution with 20 L of this mixture, the solvent ratio was switched to 1:12:12 (5 L), then 1:10:10, resulting in the recovery of 4.40 g of the dimer. Further elution with a mixing ratio of 1:8:8 gave 1.04 g of crude trimer (purity 90% by HPLC).

The crude trimer and the trimer/tetramer mixture were each dissolved in methyl cyanide (CH$_3$CN) and separated by preparative HPLC (column D; 0–30 minutes, 80 to 100% CH$_3$CN in water, then CH$_3$CN); the retention times for the dimer, trimer, and tetramer were 22.5 (22.7), 30.1 (30.8), and 33.9 minutes, respectively. After combination of appropriate fractions, evaporation, and drying in vacuo, the following yields were obtained: bis(5,7,3',4'-tetra-O-benzyl)epicatechin 4β,8)-dimer, 4.43 g (79% recovery); tris(5,7,3',4'-tetra-O-benzyl)epicatechin (4β,8)$_2$-trimer, 1.13 g (40%); tetrakis-(5,7,3',4'-tetra-O-benzyl)epicatechin (4β,8)$_3$ tetramer, 0.24 g (13%).

Example 4

Preparation of 4-[(2-Benzothiazolyl)thio]-5,7,3',4'-tetra-O-benzylepicatechin

To a solution of 6.5 g (39 mmol) of 2-mercaptobenzothiazole in 40 mL of 1,2-dichloroethan [HPLC grade, filtered over basic alumina (activity I) immediately before use] was added dropwise in 10 minutes under nitrogen with ice cooling and stirring 19.5 mL of trimethylaluminum solution (2.0 M in toluene). The resulting amber solution was stirred at 0° C. for 15 minutes, then a solution of 5.56 g (7.82 mmol) of 5,7,3',4',-tetra-O-benzyl-4-(2-hydroxyethoxy)epicatechin in 60 mL of 1,2-dichloroethane (pretreated as above) was added dropwise in 20 minutes. The orange-colored reaction mixture was stirred at room temperature for 5 hours, then cooled in an ice bath, and a solution of 22.6 g (80 mmol) of potassium sodium tartrate tetrahydrate in 90 mL of water and 100 mL of 2.5 M aqueous sodium hydroxide was added dropwise (very cautiously at first because of gas evolution). Methylene chloride (100 mL) was added, and the phases were separated. The organic phase was washed two times with 100 mL of 2.5 M aqueous sodium hydroxide and dried over sodium sulfate. After evaporation to a small volume, the residue was chromatographed on a short silica gel column with ethyl acetate/toluene 1:19 (until the beginning elution of product), then 1:9. The eluate was evaporated to yield an oil, which soon turned into a light-yellow solid. This material was dissolved in 30 mL of hot ethyl acetate, 90 mL of 1-chlorobutane was added, and the solution was seeded and set aside for crystallization first at room temperature, then at −20° C. The precipitate was isolated by suction filtration, washed two times with 20 mL of cold 1-chlorobutane, and dried in vacuo to yield 3.50 g of the predominant diastereoisomer. Chromatography of the mother liquor (silica gel, ethyl acetate/methylene chloride/hexane 1:18:11 to 2:18:11) followed by crystallization from ethyl acetate/1-chlorobutane yielded an additional 0.78 g of the major isomer (together 4.28 g, 67%) and 0.16 g (2.5%) of the less polar minor isomer.

Major diastereoisomer: mp 160–161° C. (from ethylacetate/1-chlorobutane); $[\alpha]_D$+106°, $[\alpha]_{546}$+133° (EtOAc, c 10.6 gL$^{-1}$); $^1$H NMR (CDCl$_3$) δ 7.89 (ddd, 1 H, J=8, 1.2, 0.7 Hz), 7.78 (ddd, 1 H, J=8, 1.2, 0.7 Hz), 7.47–7.20 (m, 19 H), 7.17 (d, 1 H, J=2 Hz), 7.12–7.00 (m, 4 H), 6.95 (B part of an ABq, 1 H, J=8.5 Hz), 6.30, 6.29 (ABq, 2 H, J=2 Hz), 5.46 (d, 1 H, J=2 Hz),5.42 (s, 1 H), 5.17 (s, 2 H), 5.16 (s, 2 H),5.10, 5.05 (ABq, 2 H, J=12 Hz), 5.03 (s, 2 H), 4.40 (ddd, 1 H, J=6, 2.5, 1 Hz), 2.00 (d, 1 H, J=5.5 Hz); $^{13}$C NMR (CDCl$_3$) δ 165.00, 160.67, 158.76, 155.95, 153.16, 148.96, 148.88, 137.17, 137.07, 136.53, 136.47, 135.29, 130.76, 128.61, 128.45, 128.37, 128.16, 128.09, 127.75, 127.56, 127.49, 127.46, 127.21, 126.57, 126.06, 124.41, 121.83, 120.97, 119.65, 114.91, 113.58, 98.34, 94.48, 75.13, 71.32, 71.22, 70.78, 70.13, 69.86, 44.43; IR (film) 3554 (br), 1617, 1591, 1177, 1152, 1114, 735, 696 cm$^{-1}$. Analysis Calcd for $C_{50}H_{41}NO_6S_2$: C, 73.60; H, 5.06; N, 1.72. Found: C, 73.92; H, 4.75; N, 1.74.

Minor diastereoisomer: mp 144–146° C. (from ethyl acetate/1-chlorobutane); $[\alpha]_D$ –48.9°, $[\alpha]_{546}$ –64.6° (EtOAc, c 7.6 gL$^{-1}$); $^1$H NMR (CDCl$_3$) δ 7.79 (ddd, 1 H, J=8, 1.2, 0.7 Hz), 7.66 (ddd, 1 H, J=8, 1.2, 0.7 Hz), 7.47–7.25 (m, 14 H), 7.17–7.11 (m, 2 H), 7.08–6.89 (m, 5 H), 6.84–6.77 (m, 4 H), 6.27, 6.25 (ABq, 2 H, J=2 Hz), 5.45–5.40 (m, 2 H), 5.16 (narrow ABq, 2 H), 5.11, 5.07 (ABq, 2 H, J=13 Hz), 5.07, 5.03 (ABq, 2 H, J=11.5 Hz), 4.94, 4.87 (ABq, 2 H, J=11.5Hz), 4.78 (q, 1 H, J=5Hz), 4.39 (d, 1 H, J=5 Hz); $^1$H NMR (C$_6$D$_6$) δ 7.68 (d, 1 H, J=8 Hz), 7.38 (d, 1 H, J=2 Hz), 7.32–6.96 (m, 19 H), 6.90–6.68 (m, 6 H), 6.48 (d, 1 H, J=2 Hz), 6.22 (d, 1 H, J=2.5 Hz), 5.82 (dd, 1 H,J=5, 1.2 Hz), 5.57 (d, 1 H, J=4.5 Hz), 4.95 (s, 2 H), 4.82 (q, 1 H, J=4.5 Hz), 4.80 (s, 2 H), 4.71 (s, 2 H), 4.70 (d, 1 H, partly concealed), 4.58, 4.51 (ABq, 2 H, J=12 Hz); $^{13}$C NMR (CDCl$_3$) δ 169.70, 160.84, 158.13, 155.45, 152.30, 148.53, 148.14, 137.14, 137.02, 136.41, 135.88, 135.44, 129.67, 128.58, 128.36, 128.16, 128.08, 127.87, 127.65, 127.55, 127.35, 127.31, 127.22, 127.00, 126.70, 125.89, 124.15, 121.23, 120.85, 119.74, 114.41, 114.31, 100.87, 93.80, 93.76, 76.46, 71.01, 70.73, 70.06, 70.00, 68.02, 46.51; IR (film) 3440 (br), 1614, 1584, 1154, 1122, 752, 732, 696 cm$^{-1}$. Analysis: Calculated for $C_{50}H_{41}NO_6S_2$: C, 73.60; H, 5.06; N, 1.72. Found: C, 73.22; H, 4.64; N, 1.71.

The above reaction should be conducted in a well-ventilated fume hood because although 2-mercaptobenzothiazole is odorless, small quantities of malodorous (but not very volatile) 2-(benzylthio) benzothiazole was formed in this reaction.

Example 5

Preparation of 3-O-Acetyl-4-[(2-benzothiazolyl) thiol]-5,7,3',4'-tetra-O-benzylepicatechin To a solution of 3.50 g (4.29 mmol) of 4-[(2-benzothiazolyl)thio]-5,7,3',4'-tetra-O-benzylepicatechin (major diastereomer from Example 4) and 53 mg (0.43 mmol) of 4-(dimethylamino)pyridine in 12 mL of anhydrous pyridine was added all at once 2.0 mL (21.5 mmol) of acetic anhydride. The reaction mixture was kept at room temperature in a closed flask for 50 hours. Ice and 150 mL of 5% aqueous hydrochloric acid were added. The product was extracted into 100+20 mL of methylene chloride. The combined organic phases were washed with 100 mL of water and two times with 50 mL of 10% aqueous sodium hydroxide; after each washing, the aqueous phase was back-extracted with 20 mL of methylene chloride. The combined organic phases were dried over magnesium sulfate and evaporated and the residue was taken up in a small volume of toluene and filtered over silica gel with ethyl acetate/hexane (1:3). Evaporation and drying in vacuo yielded 3.58 g (97%) 3-O-acetyl-4-[(2-benzothiazolyl)thio]-5,7,3',4'-tetra-O-benzylepicatechin as a yellowish foam: $[\alpha]_D$ +91.7°, $[\alpha]_{546}$+ 115° (EtOAc, c 13.2 gL$^{-1}$); $^1$H NMR (CDCl$_3$) δ 7.90 (d, 1 H, J=8 Hz), 7.77 (d, 1 H, J=8 Hz), 7.46–7.22 (m, 19 H), 7.11 (d, 1 H, J=2 Hz), 7.09–7.00 (m, 3 H), 6.99, 6.91 (ABq, 2 H, J=8.5 Hz, A part d with J=2 Hz), 6.31, 6.30 (ABq, 2 H, J=2.5 Hz), 5.63 (dd, 1 H, J=2.5, 1.2 Hz), 5.55 (s, 1 H), 5.31 (d, 1 H, J=2 Hz), 5.17, 5.12 (ABq, 2 H,J=12 Hz), 5.14 (s, 2 H), 5.10, 5.05 (ABq, 2 H, J not readable because of overlap), 5.07, 5.02 (ABq, 2 H, J=11.5 Hz), 1.84 (s, 3 H); $^{13}$C NMR (CDCl$_3$, TMS) δ 169.08, 164.07, 160.69, 158.31, 156.03, 153.22, 148.92, 148.89, 137.18, 137.16, 136.53, 136.31, 135.62, 130.29, 128.67, 128.45, 128.24, 128.19, 127.78, 127.65, 127.43, 127.31, 126.87, 126.10, 124.50, 122.16, 121.01, 119.80, 114.97, 113.51, 98.50, 94.46, 94.30, 74.13, 71.44, 71.23, 70.74, 70.19, 70.13, 42.59, 20.84; IR 1750, 1616, 1591, 1217, 1152, 1117, 734, 696 cm$^{-1}$. Analysis: Calculated for $C_{52}H_{43}NO_7S_2$: C, 72.79; H, 5.05; N, 1.63. Found: C, 73.01; H, 4.79; N, 1.61.

Example 6

Preparation of Bis(3-O-acetyl-5,7,3',4'-tetra-O-benzyl)epicatechin (4β,8)-Dimer A solution of 1.5 mL (16 mmol) of acetic anhydride in 4 mL of anhydrous pyridine was added all at once to 3.69 g (2.84 mmol) of bis(5,7,3',4'-tetra-O-benzyl)epicatechin (4β, 8)-dimer. The mixture was occasionally swirled until all starting material dissolved and then allowed to stand in a closed flask at room temperature for 99 hours. The reaction was terminated by addition of 30 mL of ethyl acetate and 2 mL of methanol and allowed to stand at room temperature for 1.5 hours. Another 20 mL of ethyl acetate was added. Then the solution was washed with 200 mL of 0.5 M aqueous phosphoric acid (H$_3$PO$_4$). The aqueous layer was back-extracted with 50 mL of ethyl acetate. The combined organic phases were dried over magnesium sulfate. After evaporation, the residue was taken up in a small volume of toluene and chromatographed on a short silica gel column with ethyl acetate/hexane (1:9, then 1:3, finally 1:1). Evaporation and drying in vacuo yielded 3.82 g (97%) of bis(3-O-acetyl-5,7,3',4'-tetra-O-benzyl)epicatechin (4β,8)-dimer as a colorless foam.

Example 7

Reaction of 3-O-Acetyl-4-[(2-benzothiazolyl)thio]-5,7,3',4'-tetra-O-benzylepicatechin with Bis(3-O-acetyl-5,7,3',4'-tetra-O-benzyl)epicatechin (4β,8)-Dimer A 0.80 g (4.1 mmol) sample of silver tetrafluoroborate (AgBF$_4$) was dried in the reaction flask at 100° C. in an oil pump vacuum with exclusion of light for 1.5 hours. After cooling, the vacuum was broken with nitrogen, and a solution of 5.66 g (4.09 mmol) of bis(3-O-acetyl-5,7,3',4'-tetra-O-benzyl)epicatechin (4β,8)-dimer in 60 mL of anhydrous tetrahydrofuran was added all at once. The flask was placed in an ice bath under dim light, and a solution of 1.40 g (1.64 mmol) of 3-O-acetyl-4-[(2-benzothiazolyl)thio]-5,7, 3',4'-tetra-O-benzyleipcatechin in 30 mL of anhydrous tetrahydrofuran was added dropwise in 70 minutes with stirring. The reaction mixture turned yellow, and a turbidity eventually appeared. Stirring at 0° C. was continued for 40 minutes, during which time period the reaction mixture turned into a milky, whitish suspension. Triethylamine (1.1 mL, 8 mmol) was added, the mixture was evaporated to near dryness, and the residue was filtered over a short silica gel column with ethyl acetate/hexane 1:1. The eluate was evaporated and the crude product was analyzed by HPLC (column A; 0–30 minutes, 80 to 100% methyl cyanide (CH$_3$CN) in water, then CH$_3$CN. The following peaks were observed (assignment/area %): $t_R$ 5.0 (4-OH-monomer, 0.15), 12.6 (4-OH-dimer, 0.25), 15.6 (dimer, 59.4), 24.8 (trimer, 23.4), 30.3 (tetramer, 12.5), 33.3 (pentamer, 3.2), 35.4 (hexamer, 0.8), 37.3 (heptamer, 0.1), 39.1 minutes (octamer, 0.02). A partial separation was achieved by column chromatography on silica gel (38×9 cm). Initial elution with 25 L of ethyl acetate/chloroform/hexane (1:10:9) did not result in product recovery (this stage was, however, essential for achieving separation). Another 25 L of ethyl acetate/chloroform/hexane (1:11:8) eluted 4.01 g of the dimer (71% recovery; pure by HPLC). A fraction (1.72 g) consisting of trimer, tetramer, and some pentamer was eluted with 20 L of ethyl acetate/chloroform/hexane 1:12:7. Finally, the column was stripped with ethyl acetate/chloroform/hexane (2:12:7) to give 0.87 g of a fraction consisting mostly of the larger oligomers. The latter two fractions were taken up in methyl cyanide ($CH_3CN$) and separated in several portions by preparative HPLC (column D; 0–30 minutes, 80 to 100% $CH_3CN$ in water, then $CH_3CN$, and the appropriate fractions were pooled and dried in vacuo to obtain the oligomers as colorless films or foams. The retention times and yields relative to 3-O-acetyl-4-[(2-benzothiazolyl)thio]-5,7,3',4'-tetra-O-benzylepicatechin for the trimer through octamer were 31.9 minutes (1.46 g, 43%), 36.0 minutes (755 mg, 33%), 39.6 minutes (204 mg, 11%), 45.0 minutes (45 mg, 2.6%), 52.8 minutes (13.8 mg, 0.9%), and 64.1 minutes (5.2 mg, 0.3%), respectively; for 3-O-acetyl-5,7,3',4'-tetra-O-benzylepicatechin-(4β,8)-(3-O-acetyl-5,7,3',4'-tetra-O-benzyl-4-hydroxyepicatechin) 22.2 minutes (13.4 mg, 1.2%). The 4-OH monomer (i.e., 3-O-acetyl-5,7,3',4'-tetra-O-benzyl-4-hydroxyepicatechin) was not recovered from the silica gel column, probably because of its high polarity. The total mass balance relative to 3-O-acetyl-4-[(2-benzothiazolyl)thio]-5,7,3',4'-tetra-O-benzylepicatechin was 92%.

Example 8

Coupling of 3-O-Acetyl-4-[(2-benzothiazolyl)thio]-5,7,3',4'-tetra-O-benzylepicatechin with Tris-(3-O-acetyl-5,7,3',4'-tetra-O-benzyl)epicatechin (4β,8)$_2$-Trimer The reaction was conducted analogously to the coupling of Example 7 using 0.41 g (2.1 mmol) of silver tetrafluoroborate ($AgBF_4$), 4.40 g (2.12 mmol) of tris(3-O-acetyl-5,7,3',4'-tetra-O-benzylepicatechin (4β,8)$_2$-trimer, and 729 mg (850 μmol) of 3-O-acetyl-4-[2-(benzoyhiazolythio]-5,7,3',4'-tetra-O-benzylepicatechin. After filtration over silica gel with ethyl acetate/hexane (1:1), the crude product was taken up in methyl cyanide ($CH_3CN$) and separated in several portions by preparative HPLC as above to yield the following products: 3-O-acetyl-5,7,3',4'-tetra-O-benzyl-4-hydroxyepicatechin (31 mg, 5%); 3-O-acetyl-5,7,3',4'-tetra-O-benzylepicatechin-(4β,8)-(3-O-acetyl-5,7,3',4'-tetra-O-benzyl-4-hydroxyepicatechin (34 mg, 6%); trimer (3.07 g, 70% recovery); tetramer (1.47 g, 62%); pentamer (221 mg, 15%); hexamer (57 mg, 5%); heptamer (25.2 mg, 2%); octamer (10.8 mg, 1%). Total mass balance relative to 3-O-acetyl-4-[(2-benzothiazolyl)thio]-5,7,3',4'-tetra-O-benzylepicatechin 96%.

Example 9

Coupling of 3-O-Acetyl-4-[(2-benzothiazolyl)thio]-5,7,3',4'-tetra-O-benzylepicatechin with Tetrakis(3-O-acetyl-5,7,3',4'-tetra-O-benzyl)epicatechin (4β,8)$_3$-Tetramer The reaction was conducted analogously to the couplings of Examples 7 and 8 using 0.34 g (1.75 mmol) of silver tetrafluoroborate ($AgBF_4$), 4.77 g (1.73 mmol) of tetrakis-(3-O-acetyl-5,7,3',4'-tetra-O-benzyl)epicatechin (4β,8)$_3$-tetramer, and 592 mg (690 μmol) of 3-O-acetyl)-4-[(2-benzothiazolyl)thio]-5,7,3',4'-tetra-O-benzylepicatechin. After filtration over silica gel with ethyl acetate/hexane (1:1), the crude product was subjected in several portions to a preliminary separation by preparative HPLC (column D; 0–30 minutes, 80 to 100% methyl cyanide ($CH_3CN$) in water; 30–38 minutes, $CH_3CN$; 38–65 minutes, 10% ethyl acetyl in $CH_3CN$) to yield the following products: 3-O-acetyl-5,7,3',4'-tetra-O-benzyl-4-hydroxy epicatechin ($t_R$ 11.0 min; 19 mg, 4%); 3-O-acetyl-5,7,3',4'-tetra-O-benzylepicatechin-(4β,8)$_3$-(3-O-acetyl-5,7,3',4'-tetra-O-benzyl-4-hydroxyepicatechin (22.2 min; 47 mg, 10%); tetramer (36.0 min; 3.56 g, 74% recovery); pentamer (39.4 min; 1.03 g); hexamer (43.6 min; 260 mg); heptamer (46.0 min; 86 mg); octamer (48.9 min; 41 mg); nonamer (52.2 min; 22 mg); decamer (56.2 min; 13.5 mg); undecamer (61.4 min; 8.2 mg). All products from the pentamer on required additional purification because of peak tailing, which led to a contamination with lower oligomers that increased with the degree of oligomerization, and because of increasing contamination with unidentified aliphatic material from the nonpolar solvent and/or column. For sample preparation, a small percentage of tetrahydrofuiran had to be added to the $CH_3CN$ from the heptamer on because of limited solubility in $CH_3CN$ alone. For the pentamer through nonamer, the additional purification was performed on column D (0–30 minutes, 80 to 100% $CH_3CN$ in water, then $CH_3CN$). For the decamer and undecamer, column B was used in combination with the same gradient. The nonamer, decamer, and undecamer still contained excessive amounts of aliphatic impurities after this treatment and were subjected to a third HPLC purification on column A using the same gradient. The following yields of pure products (97% or better by HPLC) were obtained: pentamer, 987 mg (41%); hexamer, 226 mg (16%); heptamer, 68 mg (6.1%); octamer, 26 mg (2.7%); nonamer, 11.5 mg (1.3%); decamer, 6.5 mg (0.8%); undecamer, 2.5 mg (0.3%). Total mass balance relative to 3-O-acetyl-4[(2-benzothiazoyl)thio]-5,7,3',4'-tetra-O-benzylepicatechin: 82%.

Example 10

Hydrolysis of Acetyl Protecting Groups from Acetyl- and Benzyl-Protected Oligomers Part A—Tris(5,7,3',4'-tetra-O-benzyl)epicatechin (4β,8)$_2$-Trimer To a solution of 1.54 g (742 μmol) of tris(3-O-acetyl-5,7,3',4'-tetra-O-benzyl)epicatechin (4β,8)$_2$-trimer in 30 mL of tetrahydrofuran was added all at once 5.8 mL (8.9 mmol) of 40% aqueous tetra-n-butylammonium hydroxide. The reaction mixture was allowed to stand at room temperature in a closed flask for 94 hours, then partially evaporated to remove the tetrahydrofuran. The residue was diluted with 20 mL of water, the product was extracted twice with 20 mL ethyl acetate, and the combined organic phases were washed with 10 mL of brine and evaporated. Filtration over a short silica gel column with ethyl acetate yielded, after evaporation and drying in vacuo, 1.44 g (99%) of tris(5,7,3',4'-tetra-O-benzyl)epicatechin (4β,8)$_2$-trimer as a colorless foam.

Part B—Tetrakis(5,7,3',4'-tetra-O-benzyl)eipicatechin (4β,8)$_3$-Tetramer

Reaction of 1.59 g (573 μmol) of tetrakis(3-O-acetyl-5,7,3',4'-tetra-O-benzyl)epicatechin (4β,8)$_3$-tetramer with 5.6 mL (8.6 mmol) of 40% aqueous tetra-n-butyl-ammonium hydroxide in 29 mL of tetrahydrofuran for 96 hours (as described for the trimer) yielded 1.45 g (97%) of tetrakis (5,7,3',4'-tetra-O-benzyl)epicatechin (4β,8)$_3$-tetramer as a colorless foam.

Part C—Pentakis(5,7,3',4'-tetra-O-benzyl)epicatechin (4β,8)$_4$-Pentamer

Reaction of 1.81 g (524 μmol) of pentakis(3-O-acetyl-5,7,3',4'-tetra-O-benzyl)-epicatechin (4β,8)$_4$-pentamer with 6.9 mL (10.5 mmol) of 40% aqueous tetra-n-butyl-ammonium hydroxide in 35 mL of tetrahydrofuran for 118 hours, as described for the trimer, yielded 1.45 g (97%) of pentakis (5,7,3',4'-tetra-O-benzyl)epicatechin (4β,8)$_4$-pentamer as a colorless foam. The analytical sample was further purified by preparative HPLC (Column B, 0–30 min, 80–100% CH$_3$CN/H$_2$O, then CH$_3$CN.

Part D—Hexakis(5,7,3',4'-tetra-O-benzyl)epicatechin (4β,8)$_5$-Hexamer

Reaction of 486 mg (117 µmol) of hexakis(3-O-acetyl-5, 7,3',4'-tetra-O-benzyl)epicatechin (4β,8)$_5$-hexamer with 1.5 mL (2.3 mmol) of 40% aqueous tetra-n-butyl ammonium hydroxide in 8 mL of tetrahydrofuran for 101 hours (as described for the trimer) yielded 455 mg (100%) of hexakis (5,7,3',4'-tetra-O-benzyl)epicatechin (4β,8)$_5$-hexamer as a colorless glass.

Part E—Heptakis(5,7,3',4'-tetra-O-benzyl)epicatechin (4β,8)$_6$-Heptamer

Reaction of 126 mg (26.1 µmol) of heptakis(3-O-acetyl-5,7,3',4'-tetra-O-benzyl)epicatechin (4β,8)$_6$-heptamer with 0.34 mL (0.52 mmol) of 40% aqueous tetra-n-butyl-ammonium hydroxide in 1.8 mL of tetrahydroftiran for 94 hours (as described for the trimer) yielded 118 mg (100%) of heptakis(5,7,3',4'-tetra-O-benzyl)epicatechin (4β,8)$_6$-heptamer as a colorless foam.

Part F—Octakis(5,7,3', 4'-tetra-O-benzyl)epicatechin (4β,8)$_7$-Octamer

Reaction of 41.2 mg (26.1 µmol) of octakis(3-O-acetyl-5,7,3',4'-tetra-O-benzyl)epicatechin (4β,8)$_7$-octamer with 0.10 mL (0.15 mmol) of 40% aqueous tetra-n-butyl ammonium hydroxide in 0.5 mL of tetrahydrofuran for 126 hours (as described for the trimer) yielded 39.4 mg (102%) of octakis (5,7,3',4'-tetra-O-benzyl)epicatechin (4β,8)$_7$-octamer as a colorless foam.

Part G—Nonakis (5,7,3',4'-tetra-O-benzyl)epicatechin (4β,8)$_8$-Nonamer

Reaction of 17.9 mg (2.88 µmol) of nonakis (3-O-acetyl-5,7,3',4'-tetra-O-benzyl)epicatechin (4β,8)$_8$-nonamer with 47 µL (72 µmol) of 40% aqueous tetra-n-butyl ammonium hydroxide in 0.3 mL of tetrahydrofuran for 134 hours (as described for the trimer) yielded 16.8 mg (100%) of nonakis (5,7,3',4'-tetra-O-benzyl)epicatechin (4β,8)$_8$-nonamer as a colorless foam.

Example 11

Preparation of Epicatechin (4β,8)-Oligomers from Benzyl-Protected Oligomers

A. Preparation of Epicatechin (4β,8)$_2$-Trimer

To a solution of 64.3 mg (33.0 µmol) of bis(5,7,3',4'-tetra-O-benzyl)epicatechin (4β,8)-dimer in 5 mL of tetrahydrofuran were added 5 mL of methanol, 0.25 mL of water, and 57 mg of 20% Pearlman's catalyst (Pd(OH)$_2$/C). The mixture was stirred under 1 bar of hydrogen for 80 minutes and filtered over cotton. The filtration residue was washed two times with 10 mL of methanol. The combined filtrates were evaporated, and the residue was taken up in 10 mL of HPLC grade water. The solution was filtered and lyophilized to yield 32.4 mg (101%) of epicatechin (4β,8)$_2$-trimer 6H$_2$O as a fluffy, amorphous, off-white solid: [α]$_D$+70.40°, [α]$_{546}$+ 84.40° (MeOH, c 2.2 gL$^{-1}$); (ref. 4c: [α]$_D$75.20°, acetone, c 8.7 gL$^{-1}$;ref. 4d: [α]$_{578}$+90°, MeOH, c 2 gL$^{-1}$; ref. 6: [α]$_D$+76.4°, acetone, c 8.6 gL$^{-1}$; ref 19b: [α]$_{578}$+92°, H$_2$O c 1.9 gL$^{-1}$; ref. 19k: [α]$_D$+80°, MeOH, c 1.6 gL$^{-1}$); $^{13}$C NMR (CD$_3$OD, TMS; δ 60–85 region only) δ 79.73, 77.08, 73.47, 72.94, 66.84; MS (API/ES) m/z 865.0 (calcd for [M-H]$^-$: 865.2), 577.0 (6%), 288.9 (4%). Analysis: Calculated for C$_{45}$H$_{38}$O$_{18}$.6H$_2$O: C, 55.44; H, 5.17. Found: C, 55.71; H, 5.07.

B. Preparation of Epicatechin (4β,8)$_3$-Tetramer

To a solution of 56 mg (21.6 µmol) of tris(5,7,3',4'-tetra-O-benzyl)epicatechin (4β,8)$_3$-tetramer in 4 mL of tetrahydrofuran were added 4 mL of methanol, 0.2 mL of water, and 47 mg of 20% Pearlman's catalyst (Pd(OH)$_2$/C). The mixture was stirred under 1 bar of hydrogen for 75 minutes and filtered over cotton. The filtration residue was washed two times with 5 mL of methanol. The combined filtrates were diluted with 5 mL of HPLC grade water and partially evaporated to remove the organic solvents. After dilution with another 10 mL of HPLC grade water, the solution was filtered and lyophilized to yield 24.4 mg (89%) of epicatechin (4β,8)$_3$-tetramer-6H$_2$O as a fluffy, amorphous, off-white solid: [α]$_D$+93.3°, [α]$_{546}$+114° (MeOH, c 9.3 gL$^{-1}$) (ref. 4d: [α]$_{578}$+73.2°, MeOH, c 3.7 gL$^{-1}$; ref. 4j: [α]$_D$+ 59.8°, acetone, c 12 gL$^{-1}$; ref. 6: [α]$_D$+109.5°, acetone, c 12.3 gL$^{-1}$; ref. 19i: [α]$_D$+89.2°, acetone, c 9 gL$^{-1}$; ref. 19l: [α]$_D$+81°, MeOH, c 1.1 gL$^{-1}$); MS (API/ES) m/z 1153.3 (55%; calcd for [M-H]$^-$: 1153.3), 865.1 (25%), 576.9 (100%), 500.1 (30%), 288.9 (4%). Analys: Calculated for C$_{60}$H$_{50}$O$_{24}$.6H$_2$O: C, 56.96; H, 5.10. Found: C, 56.98; H, 4.83.

C. Epicatechin (4β,8)$_4$-Pentamer

To a solution of 76 mg (23.4 µmol) of pentakis(5,7,3',4'-tetra-O-benzyl)epicatechin (4β,8)$_4$-pentamer in 4 mL of tetrahydrofuran were added 4 mL of methanol, 0.2 mL of water, and 60 mg of 20% Pearlman's catalyst (Pd(OH)$_2$/C). The mixture was stirred under 1 bar of hydrogen for 2 hours and filtered over cotton. The filtration residue was washed with methanol, and the combined filtrates were partially evaporated to remove the organic solvents. The residue was diluted with 10 mL of HPLC-grade water, filtered, and lyophilized to produce 34.8 mg of epicatechin (4β,8)$_4$-pentamer as a fluffy, amorphous, off-white solid: [α]$_D$+116°, [α]$_{546}$+140° (methanol, c 8.3 gL$^{-1}$) (ref. 4d: [α]$_{578}$+96°, meOH, c 1 gL$^{-1}$; ref. 19i: [α]$_D$+102.1°, acetone, c 10 gL$^{-1}$; ref. 19l: [α]$_D$+102°, MeOH, c 1.2 gL$^{-1}$). Analysis: Calculated for C$_{75}$H$_{62}$O$_{30}$.7.5H$_2$O: C, 57.07; H, 4.92. Found: C, 56.99; H, 4.79.

D. Preparation of Epicatechin (4β,8)$_5$-Hexamer

To a solution of 92.3 mg (23.7 µmol) of hexakis(5,7,3', 4'tetra-O-benzyl)epicatechin (4β,8)$_5$-hexamer in 8 mL of tetrahydrofuran were added 8 mL of methanol, 0.4 mL of water, and 169 mg of 20% Pearlman's catalyst (Pd(OH)$_2$/C). The mixture was stirred under 1 bar of hydrogen for 50 minutes and filtered over cotton. The filtration residue was washed with methanol, and the combined filtrates were partially evaporated after addition of 10 mL of HPLC-grade water. The residue was diluted with another 20 mL of KPLC-grade water, filtered, and lyophilized to produce 47.4 mg of epicatechin (4β,8)-hexamer as a fluffy, amorphous, off-white solid: [α]$_D$+123°, [α]$_{546}$+149°, (methanol, c 8.6 gL$^{-1}$). Analysis: Calculated for C$_{90}$H$_{74}$O$_{36}$.9.2H$_2$O: C, 56.98; H, 4.91. Found: C, 56.89; H, 4.61.

E. Preparation of Epicatechin (4β,8)$_6$-Heptamer

To a solution of 87.5 mg (19.3 µmol) of heptakis (5,7,3', 4'-tetra-O-benzyl)epicatechin (4β,8)$_6$-heptamer in 8 mL of tetrahydrofuron were added 8 mL of methanol, 0.4 mL of water, and 111 mg of 20% Pearlman's catalyst (Pd(OH)$_2$/C). The mixture was stirred under 1 bar of hydrogen (H$_2$) for 1 hour and filtered over cotton. The filtration residue was washed with MeOH, and the combined filtrates were partially evaporated after addition of 10 mL of HPLC-grade H$_2$O. The residue was diluted with another 10 mL of HPLC-grade $H_2O$, filtered, and lyophilized to produce 39.3 mg of epicatechin $(4\beta,8)_6$-heptamer as a fluffy, amorphous, off-white solid: $[\alpha]_D$+134°, $[\alpha]_{546}$+164° (MeOH, c 9.6 $gL^{-1}$). Analysis: Calculated for $C_{105}H_{86}O_{42}$·$10H_2O$: C, 57.33; H, 4.86. Found: C, 57.49; H, 4.80

F. Preparation of Epicatechin $(4\beta,8)_7$-Octamer

To a solution of 35.7 mg (6.88 μmol) of octakis (5,7,3',4'-tetra-O-benzyl)epicatechin $(4\beta,8)_7$-octamer in 3 mL of tetrahydrofuran were added 3 mL of methanol, 0.15 mL of water, and 57 mg of 20% Pearlman's catalyst ($Pd(OH)_2$/C). The mixture was stirred under 1 bar of hydrogen for 55 minutes and filtered over cotton. The filtration residue was washed with methanol, and the combined filtrates were partially evaporated after addition of 10 mL of HPLC-grade water. The residue was diluted with another 10 mL of HPLC-grade water, filtered, and lyophilized to produce 17.1 mg of epicatechin $(4\beta,8)_7$-octamer as a fluffy, amorphous, off-white solid: $[\alpha]_D$+148°, $[\alpha]_{546}$+180° (methanol, c 5.2 $gL^{-1}$). Analysis: Calculated for $C_{120}H_{98}O_{48}$·$10.7H_2O$: C, 57.66; H, 4.77. Found: C, 57.68; H, 4.79.

The HPLC analyses of the purified natural and synthetic oligomers were compared. The purified natural oligomers all exhibited additional peaks, with the number of additional peaks increasing as the oligomeric size increased.

Example 12

Self-Condensation of 4-[(2-Benzothiazolyl)thio]-5,7,3',4'-tetra-O-benzylepicatechin Induced by Silver Tetrafluoroborate To a solution of 445 mg (545 μmol) of 4-[(2-benzothiazolyl)thio]-5,7,3',4'-tetra-O-benzylepicatechin (the major diastereoisomer of Example 4) in 5 mL of anhydrous tetrahydrofuran was added dropwise within 30 minutes in dim light and with magnetic stirring and ice cooling a solution of 48 mg (247 μmol) of silver tetrafluoroborate (dried at 100° C. in an oil pump vacuum with exclusion of light for 110 minutes immediately before use). Stirring at 0° C. was continued for 5 minutes, then 0.2 mL of triethylamine was added. After evaporation, the residue was prepurified by filtration over a short silica gel column with ethyl acetate/hexane (1:1) to yield 414 mg of a colorless foam. The five least polar major components of this complex mixture were isolated by preparative HPLC (column D; 0–30 minutes, 80 to 100% methyl cyanide ($CH_3CN$) in water, then $CH_3CN$. The following retention times and yields were observed: 2-mercaptobenzothiazole, $t_R$ 4.4 minutes, 19 mg; 5,7,3',4'-tetra-O-benzyl-4-(2-thioxobenzothiazol-3-yl)epicatechin, 15.4 minutes, 18 mg (4%); starting monomer, 21.4 minutes, 14 mg (3% recovery); 5,7,3',4'-tetra-O-benzylepicatechin-$(4\beta,8)$-[5,7,3',4'-tetra-O-benzyl-4-(2-thioxobenzothiazol-3-yl)epicatechin], 23.5 minutes, 7 mg (2%); 5,7,3',4'-tetra-O-benzylepicatechin-$(4\beta,8)$-[4-((2-benzothiazolyl)thio)-5,7,3',4'-tetra-O-benzylepicatechin], 27.0 minutes, 15 mg (4%).

Example 13

Self-Condensation of 4-[(2-Benzothiazolyl)thiol-5,7,3',4'-tetra-O-benzyl-epicatechin Induced by Acidic Clay To a solution of 18.0 mg (21.0 μmol) of 4-[(2-benzothiazolyl) thio]-5,7,3',4'-tetra-O-benzylepicatechin (major diastereoisomer in Example 4) in 1 mL of anhydrous methyl chloride ($CH_2Cl_2$) was added 38 mg of montmorrilonite clay sold under the tradename Bentonite K-10. The mixture was stirred at room temperature for 160 minutes, filtered, and evaporated. The residue was separated by preparative HPLC (column B; 0–30 minutes, 80 to 100% $CH_3CN$ in water, then $CH_3CN$. The following retention times and yields were observed: 2-mercaptobenzothiazole, $t_R$ 4.6 minutes, 0.6 mg; 5,7,3',4'tetra-O-benzyl-4-(2-thioxobenzothiazol-3-yl)epicatechin, 13.2 minutes, 2.0 mg (11%); starting monomer, 19.2 minutes, 2.7 mg (15% recovery); 5,7,3',4'-tetra-O-benzylepicatechin-$(4\beta,8)$-[5,7,3',4'-tetra-O-benzyl-4-(2-thixobenzothiazoll-3-yl)epicatechin], 21.5 minutes, 0.6 mg (4%); 5,7,3',4'-tetra-O-benzylepicatechin-$(4\beta,8)$-[4-((2-benzothiazol)thio)-5,7,3',4'-tetra-O-benzylepicatechin], 25.9 minutes, 1.4 mg (9%); 5,7,3',4'-tetra-O-benzylepicatechin-$4\beta,8)$-(5,7,3',4'-tetra-O-benzylepicatechin-$(4\beta, 8)$-[4-((benzothiazothiazoyl)thio)-5,7,3',4'-bis tetra-O-benzylepicatechin], 30.8 minutes, 1.2 mg (8%); 5,7,3',4'-tetra-O-benzylepicatechin-bis$(4\beta,8)$-(5,7,3',4'-tetra-O-benzlepicatechin]-4-((2-benzothiazolyl)thio)-5,7,3',4'-tetra-O-benzylepicatechin], 34.2 minutes, 0.3 mg (2%).

Example 14

Self-Condensation of 3-O-Acetyl-4-[(2-benzothiazolyl)thio]-5,7,3',4'-tetra-O-benzylepicatechin Induced by Silver Tetrafluoroborate To a solution of 355 mg (414 μmol) of 3-O-acetyl-4-[(2-benzathiazolyl)thio]-5,7,3',4'-tetra-O-benzylepicatechin 4 mL of anhydrous tetrahydrofuran was added dropwise within 40 minutes in dim light and with magnetic stirring and ice cooling a solution of 20 mg (103 μmol) of silver tetrafluoroborate dried at 90° C. in an oil pump vacuum with exclusion of light for 1 hour immediately before use. Stirring at 0° C. was continued for 10 minutes, then 0.2 mL of triethylamine was added. After evaporation, the residue was prepurified by filtration over a short silica gel column with ethyl acetate/hexane (1:1) to yield 331 mg of a colorless foam. This mixture was separated by preparative HPLC (column D; 0–30 minutes, 80 to 100% methyl cyanide ($CH_3CN$) in water, then $CH_3CN$). The following retention times and yields were observed: 2-mercaptobenzothiazole, $t_R$ 4.6 min, 6.4 mg; 3-O-acetyl-5,7,3',4'-tetra-O-benzyl-4-hydroxyepicatechin, 11.1 min., 13.2 mg (4.5%); 3-O-acetyl-5,7,3',4'-tetra-O-benzylepicatechin-$(4\beta,8)$-(3-O-acetyl-5,7,3',4'-tetra-O-benzyl-4-hydroxyepicatechin), 16.9 min, 38.3 mg (13%); starting material, 22.4 min., 156 mg. (44%); a mixture of 3-O-acetyl-5,7,3',4'-tetra-O-benzylepicatechin-$(4\beta,8)$-[3-O-acetyl-4-((2-benzothiazolyl)thio)-5,7,3',4'-tetra-O-benzylepicatechin] and 3-O-acetyl-5,7,3',4'-tetra-O-benzylepicatechin-$(4\beta,8)$-(3-O-acetyl-5,7,3',4'-tetra-O-benzylepicatechin)-$(4\beta,8)$-(3-O-acetyl-5,7,3',4'-tetra-O-benzyl-4-hydroxyepicatechin): 29.7 min, 54.3 mg; a mixture of 3-O-acetyl-5,7,3',4'-tetra-O-benzylepicatechin-$(4\beta,8)$-(3-O-acetyl-5,7,3',4'-tetra-O-benzylepicatechin)-$(4\beta,8)$-[3-O-acetyl-4-((2-benzothiazolyl)thio)-5,7,3',4'-tetra-O-benzylepicatechin] and 3-O-acetyl-5,7,3',4'-tetra-O-benzylepicatechin-bis[$(4\beta,8)$-(3-O-acetyl-5,7,3',4'-tetra-O-benzylepicatechin)]-$(4\beta,8)$-(3-O-acetyl-5,7,3',4'-tetra-O-benzyl-4-hydroxyepicatechin): 34.6 min., 11.9 mg; 3-O-acetyl-5,7,3',4'-tetra-O-benzylepicatechin-bis[$(4\beta,8)$-(3-O-acetyl-5,7,3',4-tetra-O-benzyl)epicatechin]-$(4\beta,8)$-[3-O-acetyl-4-((2-benzothiazolyl)thio)-5,7,3',4'-tetra-O-benzylepicatechin]: 38.9 min., 6.3 mg (2.1%). The mixture of 3-O-acetyl-5,7,3',4'-tetra-O-benzylepicatechin-(4β,8)-[3-O-acetyl-4-((2-benzothiazolyl)thio)-5,7,3',4'-tetra-O-benzylepicatechin] and 3-O-acetyl-5,7,3',4'-tetra-O-benzylepicatechin-(4β,8)-(3-O-acetyl-5,7,3',4'-tetra-O-benzylepicatechin)-(4β,8)-(3-O-acetyl-5,7,3',4'-tetra-O-benzyl-4-hydroxyepicatechin) was separated by normal-phase HPLC (Column F; 0–40 min, 20 to 50% ethyl acetate (EtOAc) in hexane, then 50%) to yield 43 mg (14%) of 3-O-acetyl-5,7,3',4'-tetra-O-benzylepicatechin-(4β,8)-[3-O-acetyl-4-((2-benzothiazolyl)thio)-5,7,3',4'-tetra-O-benzylepicatechin] ($t_R$ 22.1 min) and 6.4 mg (2.2%) of 3-O-acetyl-5,7,3',4'-tetra-O-benzylepicatechin-(4β,8)-(3-O-acetyl-5,7,3',4'-tetra-O-benzylepicatechin)-4β,8-(3-O-acetyl-5,7,3',4'-tetra-O-benzyl-4-hydroxyepicatechin) (tR 32.8 min.). The mixture of 3-O-acetyl-5,7,3',4'-tetra-O-benzylepicatechin-(4β,8)-(3-O-acetyl-5,7,3',4'-tetra-O-benzylepicatechin)-(4β,8)-[3-O-acetyl-4-((2-benzothiazolyl)thio)-5,7,3',4'-tetra-O-benzylepicatechin] and 3-O-acetyl-5,7,3',4'-tetra-O-benzylepicatechin-bis[(4β,8)-(3-O-acetyl-5,7,3',4'-tetra-O-benzylepicatechin)]-(4β,8)-(3-O-acetyl-5,7,3',4'-tetra-O-benzyl-4 hydroxyepicatechin) was separated on column E using the same gradient to yield 5.4 mg (1.8%) of 3-O-acetyl-5,7,3',4'-tetra-O-benzylepicatechin-(4β,8)-(3-O-acetyl-5,7,3',4'-tetra-O-benzylepicatechin)-(4β,8)-[3-O-acetyl-4-((2-benzothiazolyl)thio)-5,7,3',4'-tetra-O-benzylepicatechin] ($t_R$ 34.8 min) and 5.0 mg (1.7%) of 3-O-acetyl-5,7,3',4'-tetra-O-benzylepicatechin-bis[(4β,8)-(3-O-acetyl-5,7,3',4'-tetra-O-benzylepicatechin)]-(4β,8)-(3-O-acetyl-5,7,3',4'-tetra-O-benzyl-4-hydroxyepicatechin) ($t_R$ 42.8 min). For characterization, the products obtained by normal phase HPLC were repurified on column B (0–30 min, 80 to 100% methyl cyanide ($CH_3CN$) in water then $CH_3,CN$).

Example 15

Reaction of 3-O-Acetyl-5,7,3',4'-tetra-O-benzylepicatechin-4β,8-[3-O-acetyl-4-[(2-benzothiazolyl)thio]-5,7,3',4'-tetra-O-benzylepicatechin] with Tetrakis(3-O-acetyl-5,7,3',4'-tetra-O-benzylepicatechin) $(4β,8)_3$-Tetramer A 21 mg (0.1 1 mmol) sample of silver tetrafluoroborate was dried in the reaction flask at 100° C. in an oil pump vacuum with exclusion of light for 1 hour. After cooling, the vacuum was broken with nitrogen, and a solution of 190 mg (68.8 μmol) of tetrakis (3-O-acetyl-5,7,3',4'-tetra-O-benzyl) epicatechin $(4β,8)_3$-tetramer in 1 mL of anhydrous tetrahydrofuran was added all at once. The flask was placed in an ice bath under dim light, and a solution of 35.5 mg (22.9 μmol) of 3-O-acetyl-5,7,3',4'-tetra-O-benzylepicatechin-(4β,8)-[3-O-acetyl-4-((2-benzothiazolyl)thio)-5,7,3',4'-tetra-O-benzylepicatechin) in 0.5 mL of anhydrous tetrahydroftiran was added dropwise in 12 minutes with stirring. Stirring was continued for 5 minutes at 0° C. and for 10 minutes at room temperature. Triethylamine (0.1 mL) was added, the mixture was evaporated, and the residue was filtered over a short silica gel column with ethyl acetate/hexane (1:1). The eluate was evaporated, and the crude product mixture (230 mg) was separated by preparative HPLC (column D, 280 nm; 0–30 min, 80 to 100% methyl cyanide ($CH_3CN$) in water, then $CH_3CN$. The following retention times and yields were observed: 3-O-acetyl-5,7,3',4'-tetra-O-benzylepicatechin-(4β,8)-(3-O-acetyl-5,7,3',4'-tetra-O-benzyl-4-hydroxyepicatechin), $t_R$ 22.7 min., 21.0 mg (65%); 3-O-acetyl-5,7,3',4'-tetra-O-benzylepicatechin-bis[(4β,8)-(3-O-acetyl-5,7,3',4'-tetra-O-benzylepicatechin)]-(4β,8)-(3-O-acetyl-5,7,3',4'-tetra-O-benzyl-4-hydroxyepicatechin), 34.6 min., 0.8 mg (2.5%); tetrakis(3-O-acetyl-5,7,3',4'-tetra-O-benzyl)epicatechin $(4β,8)_3$-tetramer, 36.3 min., 176 mg (92.5% recovery); hexakis(3-O-acetyl-5,7,3',4'-tetra-O-benzyl)epicatechin $(4β,8)_5$-hexamer, 45.6 min., 11.7 mg (12%); octakis(3-O-acetyl-5,7,3',4'-tetra-O-benzyl)epicatechin$(4β,8)_7$-octamer, 1.4 mg (2.2%).

Example 16

Anticancer Activity

Cell cycle analysis of procyanidin-treated MDA MB-231 human breast cancer cells showed a $G_0/G_1$ arrest by the pentamer, no effect by the dimer or trimer, and only a slight effect by the tetramer (See Table 1).

TABLE 1

Cell Cycle Analysis of MDA MB-231 Human Breast Cancer Cells Treated with Oligomeric Procyanidins Purified from Cocoa

|  | % $G_0/G_1$ | % S | % $G_2/M$ |
|---|---|---|---|
| Control | 36.69 | 23.39 | 39.92 |
| Vehicle | 38.26 | 22.43 | 39.30 |
| Dimer (200 μg/mL; 24 hrs) | 38.13 | 22.43 | 39.45 |
| Control | 42.28 | 35.61 | 22.12 |
| Vehicle | 43.60 | 34.10 | 22.30 |
| Trimer (200 μg/mL; 24 hrs) | 43.22 | 35.98 | 20.80 |
| Control | 40.33 | 36.25 | 23.42 |
| Vehicle | 43.71 | 34.42 | 21.87 |
| Tetramer (200 μg/mL; 24 hrs) | 51.46 | 28.25 | 20.30 |
| Control | 38.33 | 21.05 | 40.61 |
| Vehicle | 37.84 | 21.39 | 40.77 |
| Pentamer (200 μg/mL; 24 hr) | 66.03 | 17.23 | 16.67 |
| Pentamer (200 μg/mL; 48 hr) | 88.31 | 6.07 | 5.62 |

The increase in $G_0/G_1$ was accompanied by a decrease of cell numbers in the S phase and in the $G_2/M$ phase.

The manner of cell death (apoptosis or necrosis) was investigated by the annexin V-fluorescein isothiocyanate (FITC) assay using Trevigen's TACS™ Annexin V-FITC kit. Cell cycle analysis of MDA MB-231 cells treated with natural and synthetic procyanidin trimer, tetramer, and pentamer is shown below. Flow cytometry of procyanidin-tested MDA MD 231 human breast cover cells using annexin V-FITC and propidium iodide (control versus 24 hour treatment with 200 μg/mL of oligomer) is shown below. A is the epicatechin $(4β,8)_2$-trimer. B is the epicatechin $(4β,8)_3$-tetramer. C is the epicatechin $(4β,8)_4$-pentamer. The lower left quadrant shows viable cells. The lower right quadrant shows early apoptic events. The upper right quadrant shows late apoptic events. The upper left quadrant shows nonviable cells.

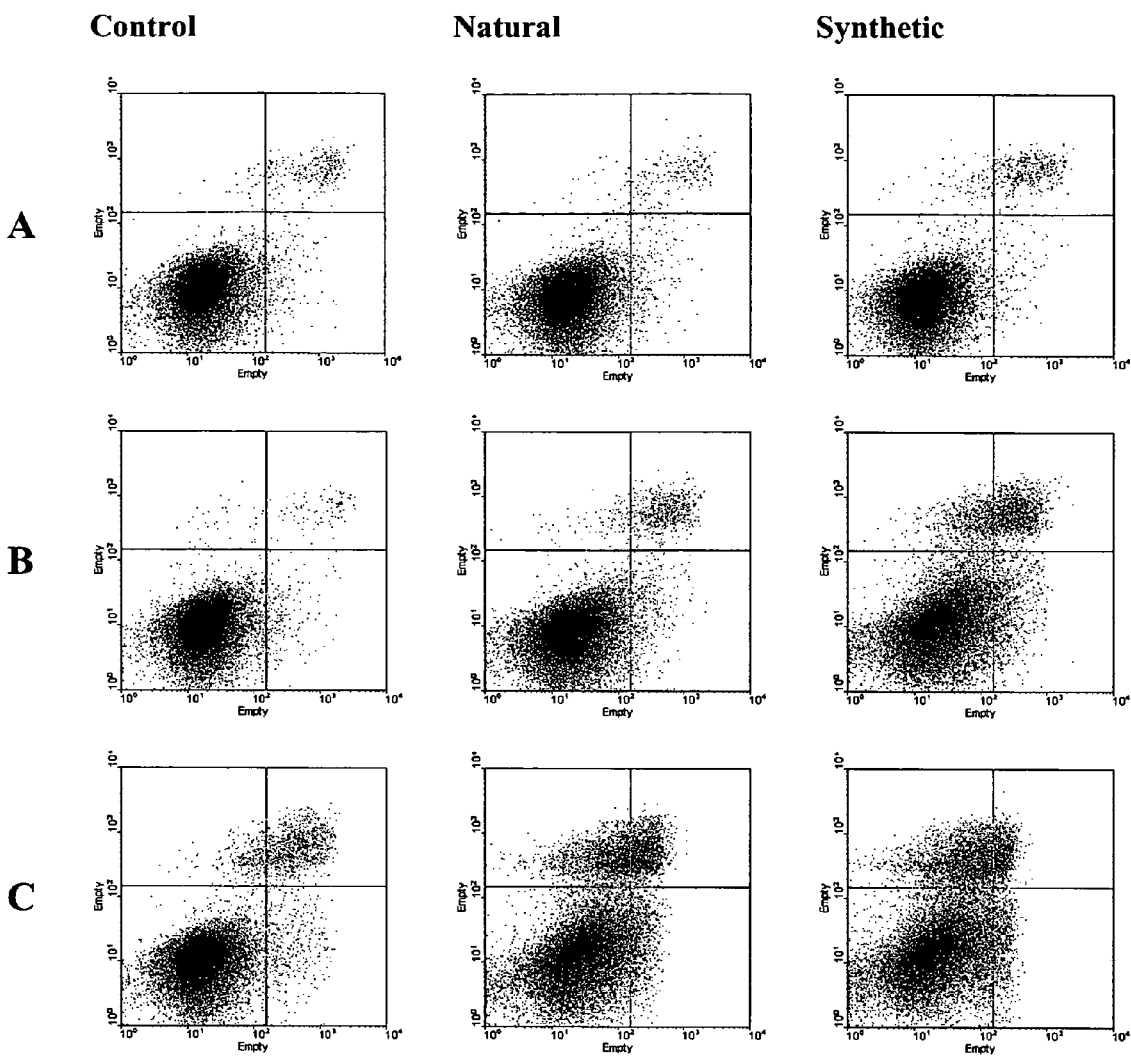

Cells treated with both natural and synthetic procyanidins showed similar profiles, with increases in cell populations in the upper right quadrant being observed as the oligomer size increased. This quadrant represents annexin V positive cells that also take up propidium iodide, which cells are considered to be in either late apoptosis or in necrosis. The absence of a distinct cell population in the lower right quadrant (cells associated with early apoptotic events) in the case of pentamer-treated cells suggests a necrotic pathway to cell death possibly due to a direct interaction with the cell membrane leading to damage, cell crisis, and eventual death.

The pentamer-caused $G_0/G_1$ arrest was reversible in cells treated up to 8 hours and irreversible after a 24 hour treatment. No difference in activity was observed between natural and synthetic procyanidin trimer. An approximately 15% increase in $G_0/G_1$ arrest was seen for synthetic procyanidin tetramer compared to natural procyanidin tetramer. An approximately 30% increase for synthetic vs. natural procyanidin pentamer was shown. See Table 2 below.

TABLE 2

Comparison Cell Cycle Analysis of MDA MB-231 Human Breast Cancer Cells Treated with Natural versus Synthetic Oligomeric Procyanidins

|  | % $G_0/G_1$ | % S | % $G_2/M$ |
|---|---|---|---|
| Control | 28.65 | 49.28 | 22.06 |
| Vehicle | 27.19 | 49.61 | 23.2 |
| Natural trimer (200 µg/mL; 24 hr) | 28.46 | 48.49 | 23.05 |
| Synthetic trimer (200 µg/mL; 24 hr) | 26.98 | 49.57 | 23.45 |
| Natural tetramer (200 µg/mL; 24 hr) | 36.82 | 43.37 | 19.02 |
| Synthetic tetramer (200 µg/mL; 24 hr) | 43.49 | 39.39 | 17.03 |
| Natural pentamer (200 µg/mL; 24 hr) | 45.99 | 38.25 | 15.76 |
| Synthetic pentamer (200 µg/mL; 24 hr) | 64.15 | 23.36 | 12.49 |

A recent report indicated that hydrogen peroxide ($H_2O_2$) was artifactually produced in vitro by several different polyphenolic compounds and was responsible for causing a variety of biological activities. See Long, L. H. et al., *Biochem. Biophys. Res. Commun.*, 2000, 273, 50. The results in Table 3 show that if hydrogen peroxide was present at the levels reported in the literature, it would produce a shift in the cell cycle to $G_2/M$ with a decrease in $G_0/G_1$. The addition of catalase abrogated these effects, causing a shift in the cell cycle back to control values. The addition of catalase alone to pentamer-treated cells produced no conclusive change in the cell cycle attributable to hydrogen peroxide, i. e., the typical $G_0/G_1$ arrest caused by the pentamer remained essentially unchanged.

To eliminate the possibility that the epicatechin $(4\beta,8)_4$-pentamer might inhibit catalase activity, hydrogen peroxide was added to pentamer-treated cells in the presence and absence of catalase. The addition of hydrogen peroxide to pentamer-treated cells led to an increase in $G_0/G_1$ and $G_2/M$ arrest at the expense of cells in the S phase. Catalase addition caused a shift back to the $G_0/G_1$ arrest typical of pentamer-treated cells, and heat-inactivated catalase had no effect. Thus, the $G_0/G_1$ arrest was directly caused by the pentamer, not by the hydrogen peroxide. These differences can be attributed to the higher purities of the synthetic procyanidins.

TABLE 3

Cell Cycle Analysis of MDA MB-231 Pentamer Treated Cells

|  | % $G_0/G_1$ | % S | % $G_2/M$ |
|---|---|---|---|
| Control | 33.14 | 44.06 | 22.81 |
| Vehicle | 36.44 | 41.63 | 21.94 |
| 100 µM $H_2O_2$; 24 hr | 20.32 | 44.92 | 34.76 |
| 100 µM $H_2O_2$ + catalase; 24 hr | 35.20 | 42.93 | 21.86 |
| 100 µM $H_2O_2$ + heat inactivated catalase; 24 hr | 20.27 | 45.48 | 34.25 |
| Control | 29.87 | 46.21 | 23.92 |
| Vehicle | 30.28 | 47.25 | 22.47 |
| Pentamers (200 µg/mL); 24 hr | 44.94 | 38.01 | 17.05 |
| Pentamers (200 µg/mL) + catalase; 24 hr | 41.23 | 39.65 | 20.12 |
| Pentamers (200 µg/mL) + heat inactivated catalase; 24 hr | 42.89 | 39.43 | 17.68 |
| Pentamers (200 µg/mL) + 100 µM $H_2O_2$; 24 hr | 42.67 | 18.63 | 38.71 |
| Pentamers (200 µg/mL) + 100 µM $H_2O_2$ + catalase; 24 hr | 48.20 | 31.12 | 20.68 |
| Pentamers (200 µg/mL) + 100 µM $H_2O_2$ + heat inactivated catalase; 24 hr | 39.47 | 23.39 | 37.14 |

Collectively, the above results confirm the cytotoxicity to human breast cancer cell lines by an epicatechin pentamer, whether purified from cocoa polyphenol extracts or prepared synthetically. The procyanidin pentamer caused a $G_0/G_1$ arrest in MDA MB-231 cells which was independent of any effects caused by hydrogen peroxide. An increase in annexin V and propidium iodide positive cells suggests that the pentamer-treated cells quickly entered into a necrotic phase of cell death.

The above examples are merely illustrative and no limitation of the preferred embodiments is implied. The skilled artisan will recognize many variations without departing from the spirit and scope of the invention.

What is claimed is:

1. A process for preparing a 5,7,3',4'-tetra-O-protected procyanidin-(4,8)-dimer comprises coupling a 5,7,3',4'-tetra-O-protected-epicatechin or -catechin monomer with a 5,7,3',4'-tetra-O-protected-4-alkoxy-epicatechin or -catechin monomer in the presence of an acidic clay.

2. The process of claim 1, wherein the protecting groups are groups which do not deactivate the A ring of the protected monomers; wherein the 4-alkoxy group is a $C_2$–$C_6$ alkoxy group having a terminal hydroxy group; and wherein the acidic clay is a Bentonite clay.

3. The process of claim 1, wherein the 5,7,3',4'-tetra-O-protected monomer is 5,7,3',4'-tetra-O-benzyl-epicatechin; wherein the 5,7,3',4'-tetra-O-benzyl-protected-4-alkoxy monomer is 5,7,3',4'-tetra-O-benzyl-4-(2-hydroxyethoxy)-epicatechin; and wherein the protected dimer is bis(5,7,3',4'-tetra-O-benzyl)-epicatechin-(4β,8)-dimer.

4. The process of claim 3, wherein the yield of the insolated dimer is about 90%.

5. The process of claim 1, wherein the coupled monomers are 5,7,3',4'-tetra-O-benzyl-epicatechin and 5,7,3',4'-tetra-O-benzyl-4-(2-hydroxyethoxy)-epicatechin and wherein the protected dimer is 5,7,3',4'-tetra-O-benzyl-epicatechin-(4β,8)-5,7,3',4'-tetra-O-benzyl-epicatechin; wherein the coupled monomers are 5,7,3',4'-tetra-O-benzyl-epicatechin and 5,7,3',4'-tetra-O-benzyl-4-(2-hydroxyethoxy)-catechin and wherein the protected dimer is 5,7,3',4'-tetra-O-benzyl-(4β,8)-5,7,3',4'-tetra-O-benzyl-catechin; and wherein the coupled monomers are 5,7,3',4'-tetra-O-benzyl-catechin and 5,7,3',4'-tetra-O-benzyl-4-(2-hydroxyethoxy)-catechin; and wherein the protected dimer is 5,7,3',4'-tetra-O-benzyl-catechin-(4α,8)-5,7,3',4'-tetra-O-benzyl-catechin.

* * * * *

UNITED STATES PATENT AND TRADEMARK OFFICE
CERTIFICATE OF CORRECTION

PATENT NO. : 7,244,855 B2
APPLICATION NO. : 10/481729
DATED : July 17, 2007
INVENTOR(S) : Kozikowski et al.

It is certified that error appears in the above-identified patent and that said Letters Patent is hereby corrected as shown below:

in Claim 4, at column 28, line 53, please rewrite "insolated" as -- isolated --

Signed and Sealed this

Seventh Day of April, 2009

JOHN DOLL
*Acting Director of the United States Patent and Trademark Office*